US007935710B2

(12) United States Patent
Van Roey et al.

(10) Patent No.: US 7,935,710 B2
(45) Date of Patent: May 3, 2011

(54) MICROBICIDAL PYRIMIDINE OR TRIAZINE FOR PREVENTING SEXUAL HIV TRANSMISSION

(75) Inventors: Jens Marcel Van Roey, Roeselare (BE); Marie-Pierre T.M. M. G. De Bethune, Everberg (BE); Paul Stoffels, Hoogstraten (BE)

(73) Assignee: Tibotec Pharmaceuticals Ltd., Co Cork (IE)

( * ) Notice: Subject to any disclaimer, the term of this patent is extended or adjusted under 35 U.S.C. 154(b) by 851 days.

(21) Appl. No.: 10/514,361

(22) PCT Filed: May 13, 2003

(86) PCT No.: PCT/EP03/50158
§ 371 (c)(1),
(2), (4) Date: May 31, 2005

(87) PCT Pub. No.: WO03/094920
PCT Pub. Date: Nov. 20, 2003

(65) Prior Publication Data
US 2006/0166943 A1    Jul. 27, 2006

(30) Foreign Application Priority Data

May 13, 2002   (EP) .................................... 02076897

(51) Int. Cl.
*A01N 43/54*   (2006.01)
*A01N 57/00*   (2006.01)
*A61K 31/505*  (2006.01)
*A61K 31/675*  (2006.01)
*C07D 239/02*  (2006.01)

(52) U.S. Cl. ........ 514/272; 514/274; 514/275; 514/269; 514/79; 544/323; 544/320; 544/316

(58) Field of Classification Search ................. 514/272, 514/274, 275, 269, 79; 544/323, 320, 316
See application file for complete search history.

(56) References Cited

U.S. PATENT DOCUMENTS

| 6,159,491 A | * | 12/2000 | Durrani ......................... 424/430 |
| 6,165,493 A |   | 12/2000 | Neurath et al. ................ 424/434 |

FOREIGN PATENT DOCUMENTS

| EP | 0945443 A1 | 9/1999 |
| EP | 1 002 795 B1 | 3/2003 |
| EP | 1 030 547 B1 | 12/2004 |
| JP | 2-196788 | 3/1990 |
| JP | 03-284624 A | 12/1991 |
| JP | 08-92252 | 9/1996 |
| WO | WO 92/01452 A1 | 2/1992 |
| WO | WO 94/01414 A1 | 1/1994 |
| WO | WO 95/06034 A1 | 3/1995 |
| WO | WO 99/50250 | 10/1999 |
| WO | WO 99/50256 | 10/1999 |
| WO | WO 9950250 A1 * | 10/1999 |
| WO | WO 00/27825 | 5/2000 |
| WO | WO 00/27828 | 5/2000 |
| WO | WO 01/22938 A1 | 4/2001 |
| WO | WO 01/85699 A2 | 11/2001 |
| WO | WO 01/85770 A2 | 11/2001 |
| WO | WO 02/08226 A2 | 1/2002 |
| WO | WO 02/070470 A2 | 9/2002 |
| WO | WO 02/076426 A2 | 10/2002 |
| WO | WO 03/016306 A1 | 2/2003 |
| WO | WO 03/062238 A1 | 7/2003 |

OTHER PUBLICATIONS

Thornton et al. Journal of Infectious Diseases, 1998. vol. 177, pp. 1608-1613.*
Piot et al. International Conference on Aids. Jun. 1989, vol. 5, No. 51. Abstract.*
Shackett, B.L. PLoS Medicine, Jan. 2008, vol. 5, No. 1, pp. 1-5.*
Ho et al. Bioorganic and Medicinal Chemistry Letters, 2009, vol. 19, pp. 6027-6031.*
Balzarini, J. et al., "Long-Term Exposure of HIV Type 1-Infected Cell Cultures to Combinations of the Novel Quinoxaline GW 420867X with Lamivudine, Abacavir, and a Variety of Non-nucleoside Reverse Transcriptase Inhibitors", *Aids Research and Human Retroviruses*, 2000, 16(6), 517-528.
Beirnaert, E. et al., Design and Evaluation of an in-House HIV-1(Group M and O) SIVmnd and SIVcpz Antigen Capture Assay, *Journal of Virological Methods*, 1998, 73, 65-70.
Christopherson, C. et al., "PCR-Based Assay to Quantify Human Immunodeficiency Virus Type 1 DNA in Peripheral Blood Mononuclear Cells", *Journal of Clinical Microbiology*, 2000, 38, 630-634.
Fabio, et al., "Vaginal Transmission of HIV-1 in hu-SCID Mice", *Aids*, 2001, 15, 2231-2238.
Fleming, D.T. et al., "From Epidemiological Synergy to Public Health Policy and Practice: The Contribution of Other Sexually Transmitted Diseases to Sexual transmission of HIV Infection", *Sexually Transmitted Infections*, 1999, 75(1), 3-17.
Geissmann, F. et al., "Transforming Growth Factor β1, in the Presence of Granulocyte/Macrophage Colony-stimulating Factor and Interleukin 4, Induces Fifferentiation of Human Peripheral Blood Monocytes into Dendritic Lagerhans Cells", *The Journal of Experimental Medicine*, 1998, 187(6), 961-966.
Peden, K, "Virological and Molecular Genetic Techniques for Studies of Established HIV Isolates", *Virological and Molecular Genetic Techniques for Studies of Established HIV Isolates*, 1995, 21-45.
Romani, N. et al., "Proliferating Dendritic Cell Progenitors in Human Blood", *The Journal of Experimental Medicine*, 1994, 180, 83-93.
Sallusto , F. et al., "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factor α", *The Journal of Experimental Medicine*, 1994, 179, 1109-1118.
Van Herrewege, Y. et al., "Activity of Reverse Transcriptase Inhibitors in Monocyte-Derived Dendritic Cells: A Possible in Vitro Model for Postexposure Prophylaxis of Sexual HIV Transmission", *Aids Research and Human Retroviruses*, 2002, 18(15), 1091-1102.

(Continued)

*Primary Examiner* — Sreeni Padmanabhan
*Assistant Examiner* — Samira Jean-Louis
(74) *Attorney, Agent, or Firm* — Woodcock Washburn LLP

(57) ABSTRACT

The present invention concerns the microbicidal activity of certain pyrimidine or triazine containing non-nucleoside reverse transcriptase inhibitors. The compounds of the present invention inhibit the systemic infection of a human being with HIV, in particular, the present compounds prevent sexual HIV transmission in humans.

19 Claims, No Drawings

OTHER PUBLICATIONS

Vanham, G., et al., "Modeling HIV Transfer Between Dendritic Cells and T Cells: Importance of HIV Phenotype, Dendritic Cell- T Cell Contact and T-Cell Activation", *AIDS*, 2000, 2299-2311.

Vanham, et al., "Dendritic Cells, Exposed to Primary. Mixed Phenotype HIV-1 Isolates Preferentially, but not Exclusively, Replicate CCR5-Using Clones", *Aids*, 2000, 14, 1874-1876.

Hendrickson, "The SCID Mouse: Relevance as an Animal Model System for Studying Human Disease," American Journal of Pathology, Dec. 1993, vol. 143, No. 6, pp. 1511-1522.

Ludovici et al., "Evolution of Anti-HIV Drug Candidates. Part 3: Diarylpyrimidine (DAPY) Analogues," Bioorganic and Medicinal Chemistry Letters, vol. 11, No. 17, pp. 2234-2239.

Mallon et al., "Monocyte-derived dendritic cells as a model for the study of HIV-1 infection: Productive infection and phenotypic changes during culture in human serum," Immunology and Cell Biology, Oct. 1999, vol. 77, pp. 442-450.

Mosier et al., "Rapid Loss of CD4+ T cells in human-PBL-SCID mice by noncytopathic HIV isolates," Science, Apr. 30, 1993, vol. 260, No. 5108, pp. 689-692.

Mosier et al., "Resistance to human immunodeficiency virus 1 infection of SCID mice reconstituted with peripheral blood leukocytes from donors vaccinated with vaccinia gp160 and recombinant gp160," Proceedings of the National Academy of Sciences of the United States of America, Mar. 1993, vol. 90, pp. 2443-2447.

\* cited by examiner

MICROBICIDAL PYRIMIDINE OR TRIAZINE FOR PREVENTING SEXUAL HIV TRANSMISSION

CROSS-REFERENCE TO RELATED APPLICATIONS

This application is the National Stage of International Application No. PCT/EP03/50158, filed May 13, 2003, which claims priority to European Patent Application No. 02076897.4, filed May 13, 2002, the entire disclosures of which are incorporated herein by reference.

The present invention concerns the microbicidal activity of certain pyrimidine or triazine containing non-nucleoside reverse transcriptase inhibitors (NNRTIs), in particular, the present invention concerns the use of pyrimidine or triazine derivatives in the manufacture of a medicament for the prevention of HIV (Human Immunodeficiency Virus) transmission or infection in humans, in particular sexual transmission. It also concerns pharmaceutical compositions adapted to be applied at the site where sexual intercourse or related intimate contact takes place.

Worldwide, the heterosexual route is the prevalent mode of transmission of AIDS. Therefore, demands have been raised for measures that block sexual spreading of the HIV infection. As there is no effective treatment or vaccine against AIDS, preventive measures are the only tools that can presently reduce transmission of Human Immunodeficiency virus (HIV). The consistent and correct use of condoms represents an effective barrier to prevent HIV transmission. However, the reduction of acquiring infection can only be significantly reduced if condoms are used for almost all sexual intercourses; a result that can not be achieved despite intensive prevention programs to increase condom use.

Development of microbicides for topical use may represent an efficacious alternative to condoms. A microbicide is any agent that kills or deactivates disease-causing microbes. According to the International Association of Physicians in AIDS CARE (IAPAC), the definition of microbicides also includes interventions that can block or prevent infection, as well as amplification of the body's natural defenses to prevent infection through sexual acts.

Ideally, microbicides should have little or no side effects at an effective microbicidal concentration. One aspect in this respect is that the drug used as microbicide should have little or no immunosuppressive activity at an effective microbicidal concentration. In addition, the ideal microbicide should sufficiently withstand varying temperatures and acceptably function within varied pH ranges (ranges of alkaline and acidic levels in the vagina). Further, it should not eliminate the natural beneficial lactobacilli that reside in the vagina and regulate vaginal health.

Studies have demonstrated that HIV transmission through direct, biological mechanisms are facilitated in a person already infected with a sexually transmitted disease (STD) (Fleming et al. Sexually Transmitted Infections (1999 February), 75(1), 3-17). Sores, lesions and inflammations caused by STDs compromise certain physical barriers to disease. For these reasons, taking measures to prevent STD transmission is a valuable strategy in the fight against HIV infection. Several microbicides in human clinical trials contain detergent-type ingredients, which may cause lesions at vaginal and cervical epithelia. Spermicidal products containing biodetergents can inactivate HIV in vitro. However, it has been shown that such biodetergents may exacerbate genital ulcers and facilitate HIV transmission when tested in vivo.

Besides surfactants, which directly act on the virus particle, drugs that block the early steps of HIV multiplication such as antiretroviral drugs are undergoing preclinical assessment. Various antiretrovirals including non-nucleoside reverse transcriptase inhibitors (NNRTIs) have been tested in vitro with varying results. To date, no evidence has been published on the in vivo effectiveness of NNRTIs as microbicidal agents.

It has now been found that the pyrimidine and triazine compounds of the present invention exhibit microbicidal activity in that these compounds have the ability to prevent the infection by HIV.

In addition, the pyrimidine and triazine compounds of the present invention also have shown microbicidal activity against STD pathogens such as *Haemophilus ducreyi*, while maintaining their compatibility with *lactobacilli* and normal vagina flora. The derived healing effect of the present compounds on the chancroids caused by *Haemophilus ducreyi*, significantly contributes to the prevention of systemic HIV infection.

EP 1002795, WO 99/50250, WO 99/50256 and WO 00/27828 disclose compounds inhibiting the replication of the HIV virus in the human T-4 cells via an interaction with the HIV reverse transcriptase enzyme.

DESCRIPTION OF THE INVENTION

The present invention concerns the use of compounds having the formula (I), (II) and (III) wherein a compound of formula (I) corresponds to

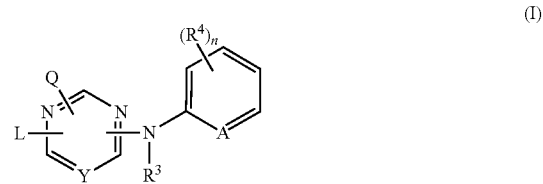

a N-oxide, a pharmaceutically acceptable addition salt or a stereochemically isomeric form thereof, wherein
Y is $CR^5$ or N;
A is CH, $CR^4$ or N;
n is 0, 1, 2, 3 or 4;
Q is —$NR^1R^2$ or when Y is $CR^5$ then Q may also be hydrogen;
$R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or
$R^1$ and $R^2$ taken together may form pyrrolidinyl, piperidinyl, morpholinyl, azido or mono- or di($C_{1-12}$alkyl)amino$C_{1-4}$alkylidene;
$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and
each $R^4$ independently is hydroxy, halo, $C_{1-6}$alkyl, $C_{1-6}$alkyloxy, cyano, amino-carbonyl, nitro, amino, trihalomethyl, trihalomethyloxy, or when Y is CR$^5$ then R$^4$ may also represent C$_{1-6}$alkyl substituted with cyano or aminocarbonyl;

R$^5$ is hydrogen or C$_{1-4}$alkyl;

L is —X$^1$—R$^6$ or —X$^2$-Alk-R$^7$ wherein
  R$^6$ and R$^7$ each independently are phenyl or phenyl substituted with one, two, three, four or five substituents each independently selected from halo, hydroxy, C$_{1-6}$alkyl, C$_{1-6}$alkyloxy, C$_{1-6}$alkylcarbonyl, C$_{1-6}$alkyloxycarbonyl, formyl, cyano, nitro, amino, and trifluoromethyl; or when Y is CR$^5$ then R$^6$ and R$^7$ may also be selected from phenyl substituted with one, two, three, four or five substituents each independently selected from aminocarbonyl, trihalomethyloxy and trihalomethyl; or when Y is N then R$^6$ and R$^7$ may also be selected from indanyl or indolyl, each of said indanyl or indolyl may be substituted with one, two, three, four or five substituents each independently selected from halo, hydroxy, C$_{1-6}$alkyl, C$_{1-6}$alkyl-oxy, C$_{1-6}$alkylcarbonyl, C$_{1-6}$alkyloxycarbonyl, formyl, cyano, nitro, amino, and trifluoromethyl; when R$^6$ is optionally substituted indanyl or indolyl, it is preferably attached to the remainder of the molecule via the fused phenyl ring. For instance, R$^6$ is suitably 4-, 5-, 6- or 7-indolyl;
  X$^1$ and X$^2$ are each independently —NR$^3$—, —NH—NH—, —N=N—, —O—, —S—, —S(=O)— or —S(=O)$_2$—;
  Alk is C$_{1-4}$alkanediyl; or
when Y is CR$^5$ then L may also be selected from C$_{1-10}$alkyl, C$_{3-10}$alkenyl, C$_{3-10}$alkynyl, C$_{3-7}$cycloalkyl, or C$_{1-10}$alkyl substituted with one or two substituents independently selected from C$_{3-7}$cycloalkyl, indanyl, indolyl and phenyl, wherein said phenyl, indanyl and indolyl may be substituted with one, two, three, four or where possible five substituents each independently selected from halo, hydroxy, C$_{1-6}$alkyl, C$_{1-6}$alkyloxy, cyano, aminocarbonyl, C$_{1-6}$alkyloxycarbonyl, formyl, nitro, amino, trihalomethyl, trihalomethyloxy and C$_{1-6}$alkylcarbonyl;

aryl is phenyl or phenyl substituted with one, two, three, four or five substituents each independently selected from halo, C$_{1-6}$alkyl, C$_{1-6}$alkyloxy, cyano, nitro and trifluoromethyl;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic hetero-cyclic radical is selected from pyrrolyl, furanyl, thienyl, pyridyl, pyrimidinyl, pyrazinyl and pyridazinyl wherein each of said aromatic heterocyclic radical may optionally be substituted with hydroxy;

and, wherein a compound of formula (II) corresponds to

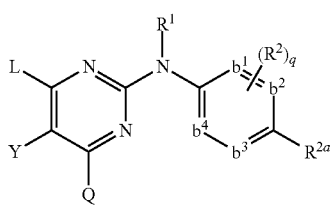

(II)

a N-oxide, a pharmaceutically acceptable addition salt, quaternary amine and the stereochemically isomeric forms thereof, wherein -b$^1$=b$^2$-C(R$^{2a}$)=b$^3$-b$^4$= represents a bivalent radical of formula —CH=CH—C(R$^{2a}$)=CH—CH=    (b-1);

—N=CH—C(R$^{2a}$)=CH—CH=    (b-2);

—CH=N—C(R$^{2a}$)=CH—CH=    (b-3);

—N=CH—C(R$^{2a}$)=N—CH=    (b-4);

—N=CH—C(R$^{2a}$)=CH—N=    (b-5);

—CH=N—C(R$^{2a}$)=N—CH=    (b-6);

—N=N—C(R$^{2a}$)=CH—CH=    (b-7);

q is 0, 1, 2; or where possible q is 3 or 4;

R$^1$ is hydrogen, aryl, formyl, C$_{1-6}$alkylcarbonyl, C$_{1-6}$alkyl, C$_{1-6}$alkyloxycarbonyl, C$_{1-6}$alkyl substituted with formyl, C$_{1-6}$alkylcarbonyl, C$_{1-6}$alkyloxycarbonyl;

R$^{2a}$ is cyano, aminocarbonyl, mono- or di(methyl)aminocarbonyl, C$_{1-6}$alkyl substituted with cyano, aminocarbonyl or mono- or di(methyl)aminocarbonyl, C$_{2-6}$alkenyl substituted with cyano, or C$_{2-6}$alkynyl substituted with cyano;

each R$^2$ independently is hydroxy, halo, C$_{1-6}$alkyl optionally substituted with cyano or —C(=O)R$^6$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

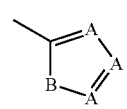

(c)

wherein each A independently is N, CH or CR$^6$;
B is NH, O, S or NR$^6$;
p is 1 or 2; and
R$^6$ is methyl, amino, mono- or dimethylamino or polyhalomethyl;

L is C$_{1-10}$alkyl, C$_{2-10}$alkenyl, C$_{2-10}$alkynyl, C$_{3-7}$cycloalkyl, whereby each of said aliphatic group may be substituted with one or two substituents independently selected from C$_{3-7}$cycloalkyl,
  indolyl or isoindolyl, each optionally substituted with one, two, three or four substituents each independently selected from halo, C$_{1-6}$alkyl, hydroxy, C$_{1-6}$alkyloxy, cyano, aminocarbonyl, nitro, amino, polyhalomethyl, polyhalomethyloxy and C$_{1-6}$alkylcarbonyl,
  phenyl, pyridinyl, pyrimidinyl, pyrazinyl or pyridazinyl, wherein each of said aromatic rings may optionally be substituted with one, two, three, four or five substituents each independently selected from the substituents defined in R$^2$; or L is —X—R$^3$ wherein
  R$^3$ is phenyl, pyridinyl, pyrimidinyl, pyrazinyl or pyridazinyl, wherein each of said aromatic rings may optionally be substituted with one, two, three, four or five substituents each independently selected from the substituents defined in R$^2$; and X is —NR¹—, —NH—NH—, —N=N—, —O—, —C(=O)—, —CHOH—, —S—, —S(=O)— or —S(=O)₂—;

Q represents hydrogen, $C_{1-6}$alkyl, halo, polyhalo$C_{1-6}$alkyl or —NR⁴R⁵; and R⁴ and R⁵ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, —S(=O)$_p$R⁶, —NH—S(=O)$_p$R⁶, —C(=O)R⁶, —NHC(=O)H, —C(=O)NHNH₂, —NHC(=O)R⁶, —C(=NH)R⁶, aryl and Het; or R⁴ and R⁵ taken together may form pyrrolidinyl, piperidinyl, morpholinyl, azido or mono- or di($C_{1-12}$alkyl)amino$C_{1-4}$alkylidene;

Y represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl optionally substituted with cyano or —C(=O)R⁶, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R⁶, —NH—S(=O)$_p$R⁶, —C(=O)R⁶, —NHC(=O)H, —C(=O)NHNH₂, —NHC(=O)R⁶, —C(=NH)R⁶ or aryl;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy; Het is meant to include all the possible isomeric forms of the heterocycles mentioned in the definition of Het, for instance, pyrrolyl also includes 2H-pyrrolyl; the Het radical may be attached to the remainder of the molecule of formula (II) through any ring carbon or heteroatom as appropriate, thus, for example, when the heterocycle is pyridinyl, it may be 2-pyridinyl, 3-pyridinyl or 4-pyridinyl;

and, wherein a compound of formula (III) corresponds to

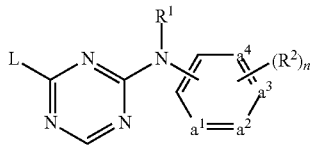

(III)

a N-oxide, a pharmaceutically acceptable addition salt, quaternary amine and the stereochemically isomeric forms thereof, wherein -a¹=a²-a³=a⁴- represents a bivalent radical of formula —CH=CH—CH=CH— (a-1);
—N=CH—CH=CH— (a-2);
—N=CH—N=CH— (a-3);
—N=CH—CH=N— (a-4);
—N=N—CH=CH— (a-5);

n is 0, 1, 2, 3 or 4; and in case -a¹=a²-a³=a⁴- is (a-1), then n may also be 5;

R¹ is hydrogen, aryl, formyl, $C_{1-4}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl; and each R² independently is hydroxy, halo, $C_{1-6}$alkyl optionally substituted with cyano or —C(=O)R⁴, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R⁴, —NH—S(=O)$_p$R⁴, —C(=O)R⁴, —NHC(=O)H, —C(=O)NHNH₂, —NHC(=O)R⁴, —C(=NH)R⁴ or a radical of formula

(c)

wherein each A independently is N, CH or CR⁴;
B is NH, O, S or NR⁴;
p is 1 or 2; and
R⁴ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, whereby each of said aliphatic group may be substituted with one or two substituents independently selected from $C_{3-7}$cycloalkyl,
  indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl,
  phenyl, pyridinyl, pyrimidinyl, pyrazinyl or pyridazinyl, wherein each of said aromatic rings may optionally be substituted with one, two, three, four or five substituents each independently selected from the substituents defined in R²; or L is —X—R³ wherein
  R³ is phenyl, pyridinyl, pyrimidinyl, pyrazinyl or pyridazinyl, wherein each of said aromatic rings may optionally be substituted with one, two, three, four or five substituents each independently selected from the substituents defined in R²; and
  X is —NR¹—, —NH—NH—, —N=N—, —O—, —C(=O)—, —CHOH—, —S—, —S(=O)— or —S(=O)₂—;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

with the proviso that compounds of formula (III) wherein
  L is $C_{1-3}$alkyl; R¹ is selected from hydrogen, ethyl and methyl; -a¹=a²-a³=a⁴—represents a bivalent radical of formula (a-1); n is 0 or 1 and R² is selected from fluoro, chloro, methyl, trifluoromethyl, ethyloxy and nitro; or L is —X—R³, X is —NH—; R¹ is hydrogen; -a¹=a²-a³=a⁴- represents a bivalent radical of formula (a-1); n is 0 or 1 and R² is selected from chloro, methyl, methyloxy, cyano, amino and nitro and R³ is phenyl, optionally substituted with one substituent selected from chloro, methyl, methyloxy, cyano, amino and nitro;

and the compounds
N,N'-dipyridinyl-(1,3,5)-triazine-2,4-diamine;
(4-chloro-phenyl)-(4(1-(4-isobutyl-phenyl)-ethyl)-(1,3,5) triazin-2-yl)-amine are not included;

in the manufacture of a medicament useful for preventing the transmission of or infection with HIV, particularly via sexual intercourse or related intimate contact between partners. In particular, the use of a compound of formula (I), (II) or (III) in the manufacture of a topical medicament useful for preventing the transmission of or infection with HIV.

Thus, the present invention also concerns a method to prevent the transmission of or infection with HIV, particularly via sexual intercourse or related intimate contact between partners, which method comprises administering, in particular topically administering, to a human an effective amount, in particular a microbicidal effective amount, of a microbicidal compound of formula (I), formula (II) or formula (III).

Suitably, the present invention concerns the use of a compound of formula (I), (II) or (III) in the manufacture of a microbicidal medicament useful for preventing the transmission of HIV wherein Y in the compound of formula (II) represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)R⁶, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R⁶, —NH—S(=O)$_p$R⁶, —C(=O)R⁶, —NHC(=O)H, —C(=O)NHNH₂, —NHC(=O)R⁶, —C(=NH)R⁶ or aryl.

The term sexual intercourse or related intimate contact between partners comprises vaginal sex, anal sex, oral sex and contact of body sites with HIV infected fluids of the sexual partner, in particular semen. Particularly, the term sexual intercourse or related intimate contact between partners constitutes vaginal, anal or oral sex, more particularly vaginal sex.

The contact sites believed to be most responsible for the transmission of HIV via sexual intercourse or related intimate contact between partners are the genitals, rectum, mouth, hands, lower abdomen, upper thighs.

The term "partners" as mentioned hereinbefore or hereinafter defines two or more warm-blooded animals, in particular humans, who are sexually active with each other, ie. who have sexual intercourse with each other or who have intimate contact with each other related to sexual activities.

In an embodiment, the present invention concerns the use of compounds having the formula (IV), wherein a compound of formula (IV) corresponds to

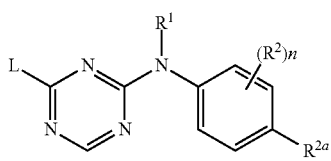

a N-oxide, a pharmaceutically acceptable addition salt, quaternary amine and the stereochemically isomeric forms thereof, wherein n is 0, 1, 2, 3 or 4;

R¹ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl; and $R^{2a}$ is cyano; aminocarbonyl; mono- or dimethylaminocarbonyl; $C_{1-6}$alkyl optionally substituted with cyano, aminocarbonyl, or mono- or dimethylaminocarbonyl; $C_{2-6}$alkenyl substituted with cyano; and $C_{2-6}$alkynyl substituted with cyano;

each R² independently is hydroxy, halo, $C_{1-6}$alkyl optionally substituted with cyano or —C(=O)R⁴, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R⁴, —NH—S(=O)$_p$R⁴, —C(=O)R⁴, —NHC(=O)H, —C(=O)NHNH₂, —NHC(=O)R⁴, —C(=NH)R⁴ or a radical of formula

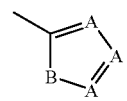

wherein each A independently is N, CH or CR⁴;
B is NH, O, S or NR⁴;
p is 1 or 2; and
R⁴ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, each of said aliphatic group substituted with phenyl, which may optionally be substituted with one, two, three, four or five substituents each independently selected from the substituents defined in R²; or L is —X—R³ wherein
R³ is phenyl, optionally substituted with one, two, three, four or five substituents each independently selected from the substituents defined in R²; and
X is —NR¹—, —NH—NH—, —N=N—, —O—, —C(=O)—, —CHOH—, —S—, —S(=O)— or —S(=O)₂—;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

with the proviso that the compound 2,4-di-p-cyanoanilino-1,3,5-triazine is not included;

in the manufacture of a microbicidal medicament useful for preventing the transmission of or infection with HIV.

Thus, the present invention also concerns a method to prevent the transmission of or infection with HIV, which method comprises administering, in particular topically administering, to a human an effective amount, in particular a microbicidal effective amount, of a microbicidal compound of formula (IV).

As used in the foregoing definitions and hereinafter halo defines fluoro, chloro, bromo and iodo; polyhalomethyl as a group or part of a group is defined as mono- or polyhalosubstituted methyl, in particular methyl with one or more fluoro atoms, for example, difluoromethyl or trifluoromethyl; polyhaloC$_{1-6}$alkyl as a group or part of a group is defined as mono- or polyhalosubstituted C$_{1-6}$alkyl, for example, the groups defined in halomethyl, 1,1-difluoro-ethyl and the like; in case more than one halogen atoms are attached to an alkyl group within the definition of polyhalomethyl or polyhaloC$_{1-6}$alkyl, they may be the same or different; C$_{1-4}$alkyl as a group or part of a group encompasses the straight and branched chained saturated hydrocarbon radicals having from 1 to 4 carbon atoms such as, for example, methyl, ethyl, propyl, butyl and the like; C$_{1-6}$alkyl as a group or part of a group encompasses the straight and branched chained saturated hydrocarbon radicals as defined in C$_{1-4}$alkyl as well as the higher homologues thereof containing 5 or 6 carbon atoms such as, for example pentyl or hexyl; C$_{1-10}$alkyl as a group or part of a group encompasses the straight and branched chained saturated hydrocarbon radicals as defined in C$_{1-6}$alkyl as well as the higher homologues thereof containing 7 to 10 carbon atoms such as, for example, heptyl, octyl, nonyl or decyl; C$_{1-12}$alkyl as a group or part of a group encompasses the straight and branched chained saturated hydrocarbon radicals as defined in C$_{1-10}$alkyl as well as the higher homologues thereof containing 11 or 12 carbon atoms such as, for example, undecyl, dodecyl and the like; C$_{1-4}$alkylidene as a group or part of a group defines bivalent straight and branched chained hydrocarbons having from 1 to 4 carbon atoms such as, for example, methylene, ethylidene, propylidene, butylidene and the like; C$_{1-4}$alkanediyl as a group or part of a group encompasses those radicals defined under C$_{1-4}$alkylidene as well as other bivalent straight and branched chained hydrocarbons having from 1 to 4 carbon atoms such as, for example, 1,2-ethanediyl, 1,3-propanediyl, 1,4-butanediyl and the like; C$_{3-7}$cycloalkyl as a group or part of a group is generic to cyclopropyl, cyclobutyl, cyclopentyl, cyclohexyl and cycloheptyl; C$_{3-10}$alkenyl as a group or part of a group defines straight and branch chained hydrocarbon radicals containing one double bond and having from 3 to 10 carbon atoms such as, for example, 2-propenyl, 2-butenyl, 2-pentenyl, 3-pentenyl, 3-methyl-2-butenyl, 3-hexenyl, 3-heptenyl, 2-octenyl, 2-nonenyl, 2-decenyl and the like, whereby the carbon atom attached to the pyrimidine ring is preferably an aliphatic carbon atom; C$_{3-10}$alkynyl as a group or part of a group defines straight and branch chained hydrocarbon radicals containing one triple bond and having from 3 to 10 carbon atoms such as, for example, 2-propynyl, 2-butynyl, 2-pentynyl, 3-pentynyl, 3-methyl-2-butynyl, 3-hexynyl, 3-heptynyl, 2-octynyl, 2-nonynyl, 2-decynyl and the like, whereby the carbon atom attached to the pyrimidine ring is preferably an aliphatic carbon atom; C$_{2-6}$alkenyl defines straight and branched chain hydrocarbon radicals having from 2 to 6 carbon atoms containing a double bond such as ethenyl, propenyl, butenyl, pentenyl, hexenyl and the like; C$_{2-10}$alkenyl defines straight and branched chain hydrocarbon radicals having from 2 to 10 carbon atoms containing a double bond such as the groups defined for C$_{2-6}$alkenyl and heptenyl, octenyl, nonenyl, decenyl and the like; C$_{2-6}$alkynyl defines straight and branched chain hydrocarbon radicals having from 2 to 6 carbon atoms containing a triple bond such as ethynyl, propynyl, butynyl, pentynyl, hexynyl and the like; C$_{2-10}$alkynyl defines straight and branched chain hydrocarbon radicals having from 2 to 10 carbon atoms containing a triple bond such as the groups defined for C$_{2-6}$alkynyl and heptynyl, octynyl, nonynyl, decynyl and the like; C$_{1-3}$alkyl as a group or part of a group encompasses the straight and branched chain saturated hydro-carbon radicals having from 1 to 3 carbon atoms such as, methyl, ethyl and propyl; C$_{4-10}$alkyl encompasses the straight and branched chain saturated hydrocarbon radicals as defined above, having from 4 to 10 carbon atoms. The term C$_{1-6}$alkyloxy defines straight or branched chain saturated hydrocarbon radicals such as methoxy, ethoxy, propyloxy, butyloxy, pentyloxy, hexyloxy, 1-methylethyloxy, 2-methylpropyloxy, 2-methylbutyloxy and the like; C$_{3-6}$cycloalkyloxy is generic to cyclopropyloxy, cyclobutyloxy, cyclopentyloxy and cyclohexyloxy.

As used herein before, the term (=O) forms a carbonyl moiety when attached to a carbon atom, a sulfoxide group when attached once to a sulfur atom, and a sulfonyl group when attached twice to a sulfur atom.

When any variable (e.g. aryl etc.) occurs more than one time in any constituent, each definition is independent.

Lines drawn into ring systems from substituents indicate that the bond may be attached to any of the suitable ring atoms. For instance for compounds of formula (I), R$^4$ can be attached to any available carbon atom of the phenyl or pyridyl ring.

For use in the presently described medicaments and methods, salts of the compounds of the present invention are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned herein above are meant to comprise the microbicidal active non-toxic addition salt forms which the compounds of the present invention are able to form. The latter can conveniently be obtained by treating the base form with such appropriate acids as inorganic acids, for example, hydrohalic acids, e.g. hydrochloric or hydrobromic acid and the like; sulfuric acid; nitric acid; phosphoric acid and the like; or organic acids, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluene-sulfonic, cyclamic, salicylic, p-aminosalicylic, pamoic and the like acids. Conversely the salt form can be converted by treatment with alkali into the free base form.

The pharmaceutically acceptable addition salts as mentioned hereinabove are also meant to comprise the microbicidal active non-toxic base forms, in particular, metal or amine addition salt forms which the compounds of the present invention are able to form. Said salts can conveniently be obtained by treating the compounds of the present invention containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely said salt forms can be converted by treatment with acid into the free acid form.

The term addition salts comprises as well the hydrates and the solvent addition forms which the compounds of the present invention are able to form. Examples of such forms are e.g. hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds wherein one or several tertiary nitrogen atoms are oxidized to the so-called N-oxide.

The term stereochemically isomeric forms of the compounds of the present invention, their N-oxides, addition salts, quaternary amines, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms that said compound may possess. Said mixture may contain all diastereomers and/or enantiomers of the basic molecular structure of said compound. All stereochemically isomeric forms of the compounds both in pure form or in admixture with each other are intended to be embraced within the scope of the present invention.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Some of the present compounds may also exist in their tautomeric forms. Such forms although not explicitly indicated in the above formula are intended to be included within the scope of the present invention.

Whenever used hereinafter, the term "compounds", the tern "compounds of the present invention" is meant to include any subgroup thereof, also the N-oxide forms, the pharmaceutically acceptable addition salts, the quaternary amines and all stereochemically isomeric forms. Of special interest are those compounds which are stereochemically pure.

Whenever substituents can be selected each independently from a list of numerous definitions, such as for example for $R^6$ and $R^7$, all possible combinations are intended which are chemically possible and which lead to chemically stable molecules.

Suitable compounds of formula (I) are those wherein Y is $CR^5$ or N; A is CH, $CR^4$ or N; n is 0, 1, 2, 3 or 4; Q is $-NR^1R^2$; $R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxy-carbonyl, aryl, amino, mono- or di($C_{1-12}$alkyl)amino, mono- or di($C_{1-12}$alkyl)amino-carbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxy-carbonyl, cyano, amino, imino, aminocarbonyl, aminocarbonylamino, mono- or di($C_{1-6}$alkyl)amino, aryl and Het; or $R^1$ and $R^2$ taken together may form pyrrolidinyl, piperidinyl, morpholinyl, azido or mono- or di($C_{1-12}$alkyl)amino$C_{1-4}$alkylidene;

$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; each $R^4$ independently is hydroxy, halo, $C_{1-6}$alkyl, $C_{1-6}$alkyloxy, cyano, aminocarbonyl, nitro, amino, trihalomethyl, trihalo-methyloxy; $R^5$ is hydrogen or $C_{1-4}$alkyl; L is $-X^1-R^6$ or $-X^2$-Alk-$R^7$ wherein $R^6$ and $R^7$ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl, $X^1$ and $X^2$ are each independently $-NR^3-$, $-NH-NH-$, $-N=N-$, $-O-$, $-S-$, $-S(=O)-$ or $-S(=O)_2-$, and Alk is $C_{1-4}$alkanediyl; aryl is phenyl or phenyl substituted with one, two, three, four or five substituents each independently selected from halo, $C_{1-6}$alkyl, $C_{1-6}$alkyloxy, cyano, nitro and trifluoromethyl; Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy.

Most preferred compounds of formula (I) are
4-[[4-amino-6-[(2,6-dichlorophenyl)methyl]-2-pyrimidinyl]amino]benzonitrile;
6-[(2,6-dichlorophenyl)methyl]-N2-(4-fluorophenyl)-2,4-pyrimidinediamine;
4-[[4-[(2,4-dichlorophenyl)methyl]-6-[(4-hydroxybutyl)amino]-2-pyrimidinyl]amino]-benzonitrile;
4-[[4-[(2,6-dichlorophenyl)methyl]-6-[(3-hydroxypropyl)amino]-2-pyrimidinyl]-amino]benzonitrile;
N-[2-[(4-cyanophenyl)amino]-6-[(2,6-dichlorophenyl)methyl]-4-pyrimidinyl]-acetamide;
N-[2-[(4-cyanophenyl)amino]-6-[(2,6-dichlorophenyl)methyl]-4-pyrimidinyl]-butanamide;
4-[[2-amino-6-(2,6-dichlorophenoxy)-4-pyrimidinyl]amino]benzonitrile;
4-[[4-[(2,6-dichlorophenyl)methyl]-6-[(2-hydroxy-2-phenylethyl)amino]-2-pyrimidinyl]amino]benzonitrile;
4-[[4-[(2,6-dichlorophenyl)methyl]-6-[[3-(2-oxo-1-pyrrolidinyl)propyl]amino]-2-pyrimidinyl]amino]benzonitrile;
4-[[4-[(2,6-dichlorophenyl)methyl]-6-[[2-(2-hydroxyethoxy)ethyl]amino]-2-pyrimidinyl]amino]benzontrile monohydrochloride;
4-[[4-[(2,6-dichlorophenyl)methyl]-6-[(2,3-dihydroxypropyl)amino]-2-pyrimidinyl]-amino]benzonitrile;
4-[[4-[(2,6-dichlorophenyl)methyl]-6-(hydroxyamino)-2-pyrimidinyl]amino]-benzonitrile;
4-[[4-[(2-cyanoethyl)amino]-6-[(2,6-dichlorophenyl)methyl]-2-pyrimidinyl]amino]-benzonitrile;
4-[[4-[(2,6-dichlorophenyl)methyl]-6-[[2-(1-pyrrolidinyl)ethyl]amino]-2-pyrimidinyl]-amino]benzonitrile;
4-[[4-amino-6-[(2,6-dichlorophenyl)methyl]-5-methyl-2-pyrimidinyl]amino]-benzonitrile;
N2-(4-bromophenyl)-6-[(2,6-dichlorophenyl)methyl]-5-methyl-2,4-pyrimidinediamine;
4-[[4-[(2,4,6-trimethylphenyl)amino]-2-pyrimidinyl]amino]benzonitrile;
4-[[2-[(2,4,6-trimethylphenyl)amino]-4-pyrimidinyl]amino]benzonitrile;
4-[[4-[(2,6-dimethylphenyl)amino]-2-pyrimidinyl]amino]benzonitrile;
4-[[4-(2,4,6-trimethylphenoxy)-2-pyrimidinyl]amino]benzonitrile;

4-[[4-[(2,6-dichlorophenyl)thio]-2-pyrimidinyl]amino]benzonitrile;
4-[[4-[[2,6-dibromo-4-(1-methylethyl)phenyl]amino]-2-pyrimidinyl]amino]benzonitrile;
4-[[4-[[2,6-dichloro-4-(trifluoromethyl)phenyl]amino]-2-pyrimidinyl]amino]-benzonitrile;
4-[[4-[(2,4-dichloro-6-methylphenyl)amino]-2-pyrimidinyl]amino]benzonitrile;
4-[[2-[(cyanophenyl)amino]-4-pyrimidinyl]amino]-3,5-dimethylbenzonitrile;
4-[[4-[(2,4-dibromo-6-fluorophenyl)amino]-2-pyrimidinyl]amino]benzonitrile;
4-[[4-amino-6-[(2,6-dichlorophenyl)methyl]-5-methyl-2-pyrimidinyl]amino]-benzeneacetonitrile;
4-[[4-[methyl(2,4,6-trimethylphenyl)amino]-2-pyrimidinyl]amino]benzonitrile;
4-[[4-[(2,4,6-trichlorophenyl)amino]-2-pyrimidinyl]amino]benzonitrile;
4-[[4-[(2,4,6-trimethylphenyl)thio]-2-pyrimidinyl]amino]benzonitrile;
4-[[4-[(2,4,6-trimethylphenyl)amino]-2-pyrimidinyl]amino]benzonitrile;
4-[[4-amino-6-[(2,4,6-trimethylphenyl)amino]-2-pyrimidinyl]amino]benzonitrile;
4-[[2-amino-6-[(2,4,6-trimethylphenyl)amino]-4-pyrimidinyl]amino]benzonitrile;
4-[[4-(2-bromo-4-chloro-6-methylphenoxy)-2-pyrimidinyl]amino]benzonitrile;
4-[[4-[(4-chloro-2,6-dimethylphenyl)amino]-2-pyrimidinyl]amino]benzonitrile;
3,5-dichloro-4-[[2-[(4-cyanophenyl)amino]-4-pyrimidinyl]amino]benzonitrile;
4-[[4-[[2,6-dichloro-4-(trifluoromethoxy)phenyl]amino]-2-pyrimidinyl]amino]-benzonitrile;
4-[[4-[(2,4-dibromo-3,6-dichlorophenyl)amino]-2-pyrimidinyl]amino]benzonitrile;
4-[[4-[(2,6-dibromo-4-propylphenyl)amino]-2-pyrimidinyl]amino]benzonitrile;
4-[[4-[(2,4,6-trimethylphenyl)amino]-2-pyrimidinyl]amino]benzamide;
4-[[4-[(4-(1,1-dimethylethyl)-2,6-dimethylphenyl)amino]-2-pyrimidinyl]amino]-benzonitrile;
4-[[2-[(4-cyanophenyl)amino]-4-pyrimidinyl]oxy]-3,5-dimethylbenzonitrile;
4-[[4-[(4-chloro-2,6-dimethylphenyl)amino]-5-methyl-2-pyrimidinyl]amino]-benzonitrile;
4-[[2-[(4-cyanophenyl)amino]-5-methyl-4-pyrimidinyl]amino]-3,5-dimethylbenzonitrile;
4-[[4-[[4-(1,1-dimethylethyl)-2,6-dimethylphenyl]amino]-5-methyl-2-pyrimidinyl]-amino]benzonitrile;
4-[[4-[(4-bromo-2,6-dimethylphenyl)amino]-5-methyl-2-pyrimidinyl]amino]-benzonitrile;
4-[[5-methyl-4-[(2,4,6-trimethylphenyl)thio]-2-pyrimidinyl]amino]benzonitrile;
4-[[4-[(2,6-dibromo-4-propylphenyl)amino]-5-methyl-2-pyrimidinyl]amino]-benzonitrile;
4-[[4-[(2,4,6-trimethylphenyl)amino]-2-pyrimidinyl]amino]benzamide, N3-oxide;
N2-(4-chlorophenyl)-N4-(2,4,6-trimethylphenyl)-2,4-pyrimidinediamine;
4-[[4-[[2,6-dibromo-4-(1-methylethyl)phenyl]amino]-5-methyl-2-pyrimidinyl]amino]-benzonitrile;
4-[[2-[(4-cyanophenyl)amino]-5-methyl-4-pyrimidinyl]amino]-3,5-dimethylbenzonitrile;
4-[[4-[(phenylmethyl)amino]-2-pyrimidinyl]amino]benzonitrile;
4-[[4-amino-6-(2,6-dimethylphenoxy)-1,3,5-triazin-2-yl]amino]benzonitrile;
4-[[4-amino-6-[(2-chloro-6-methylphenyl)amino]-1,3,5-triazin-2-yl]amino]benzonitrile;
4-[[4-amino-6-[(2,4,6-trimethylphenyl)amino]-1,3,5-triazin-2-yl]amino]benzonitrile;
4-[[4-(hydroxyamino)-6-[(2,4,6-trimethylphenyl)amino]-1,3,5-triazin-2-yl]amino]-benzonitrile;
4-[[4-amino-6-[(2-ethyl-6-methylphenyl)amino]-1,3,5-triazin-2-yl]amino]benzonitrile;
4-[[4-amino-6-[(2,6-dichlorophenyl)thio]-1,3,5-triazin-2-yl]amino]benzonitrile;
4-[[4-(hydroxyamino)-6-[(2,4,6-trichlorophenyl)amino]-1,3,5-triazin-2-yl]amino]-benzonitrile;
4-[[4-amino-6-(2,4,6-trimethylphenoxy)-1,3,5-triazin-2-yl]amino]benzonitrile;
4-[[4-(hydroxyamino)-6-(2,4,6-trimethylphenoxy)-1,3,5-triazin-2-yl]amino]-benzonitrile;
4-[[4-amino-6-[(2,4-dichloro-6-methylphenyl)amino]-1,3,5-triazin-2-yl]amino]-benzonitrile;
4-[[4-[(2,4-dichloro-6-methylphenyl)amino]-6-(hydroxyamino)-1,3,5-triazin-2-yl]-amino]benzonitrile;
4-[[4-(hydroxyamino)-6-(2,4,6-trichlorophenoxy)-1,3,5-triazin-2-yl]amino]benzonitrile trifluoroacetate (1:1);
4-[[4-(4-acetyl-2,6-dimethylphenoxy)-6-amino-1,3,5-triazin-2-yl]amino]benzonitrile;
4-[[4-amino-6-(2,4,6-tribromophenoxy)-1,3,5-triazin-2-yl]amino]benzonitrile;
4-[[4-amino-6-(4-nitro-2,6-dimethylphenoxy)-1,3,5-triazin-2-yl]amino]benzonitrile;
4-[[4-amino-6-(2,6-dibromo-4-methylphenoxy)-1,3,5-triazin-2-yl]amino]benzonitrile;
4-[[4-amino-6-(4-formyl-2,6-dimethylphenoxy)-1,3,5-triazin-2-yl]amino]benzonitrile;
4-[[4-amino-6-[(2,4-dichlorophenyl)thio]-1,3,5-triazin-2-yl]amino]benzonitrile;
4-[[4-[(5-acetyl-2,3-dihydro-7-methyl-1H-inden-4-yl)oxy]-6-amino-1,3,5-triazin-2-yl]-amino]benzonitrile;
4-[[4-amino-6-[(4-bromo-2-chloro-6-methylphenyl)amino]-1,3,5-triazin-2-yl]amino]-benzonitrile;
4-[[4-amino-6-[(2-chloro-4,6-dimethylphenyl)amino]-1,3,5-triazin-2-yl]amino]-benzonitrile;
4-[[4-amino-6-[[2,4-dichloro-6-(trifluoromethyl)phenyl]amino]-1,3,5-triazin-2-yl]-amino]benzonitrile;
4-[[4-amino-6-[methyl(2,4,6-trimethylphenyl)amino]-1,3,5-triazin-2-yl]amino]-benzonitrile;
4-[[4-amino-6-[(2,6-dibromo-4-methylphenyl)amino]-1,3,5-triazin-2-yl]amino]-benzonitrile;
4-[[4-amino-6-[[2,6-dibromo-4-(1-methylethyl)phenyl]amino]-1,3,5-triazin-2-yl]-amino]benzonitrile;
the N-oxides, the pharmaceutically acceptable addition salts and the stereochemically isomeric forms thereof.

Suitable compounds of formula (II) are those wherein one or more of the following restrictions apply:
-$b^1$=$b^2$-C($R^{2a}$)=$b^3$-$b^4$= is a radical of formula (b-1);
q is 0;
$R^{2a}$ is cyano or —C(=O)NH$_2$, preferably $R^{2a}$ is cyano;
Y is cyano, —C(=O)NH$_2$ or a halogen, preferably a halogen;
Q is hydrogen or —NR$^4$R$^5$ wherein R$^4$ and R$^5$ are preferably hydrogen;
L is —X—R$^3$ wherein X is preferably —NR$^1$—, —O— or —S—, most preferably X is —NH—, and R$^3$ is substituted phenyl with C$_{1-6}$alkyl, halogen and cyano as preferred substituents.

Another interesting group of compounds of formula (II) are those compounds wherein L is —X—R$^3$ wherein R$^3$ is 2,4,6-trisubstituted phenyl, each substituent independently selected from chloro, bromo, fluoro, cyano or $C_{1-4}$alkyl.

Also interesting are those compounds of formula (II) wherein Y is chloro or bromo and Q is hydrogen or amino.

Particular compounds are those compounds of formula (II) wherein the moiety in the 2 position of the pyrimidine ring is a 4-cyano-anilino group.

Preferred compounds are those compounds of formula (II) wherein the moiety in the 2 position of the pyrimidine ring is a 4-cyano-anilino group, L is —X—$R^3$ wherein $R^3$ is a 2,4, 6-trisubstituted phenyl, Y is a halogen and Q is hydrogen or $NH_2$.

Most preferred compounds of formula (II) are:
4-[[4-amino-5-chloro-6-[(2,4,6-trimethylphenyl)amino]-2-pyrimidinyl]amino]-benzonitrile;
4-[[5-chloro-4-[(2,4,6-trimethylphenyl)amino]-2-pyrimidinyl]amino]benzonitrile;
4-[[5-bromo-4-(4-cyano-2,6-dimethylphenoxy)-2-pyrimidinyl]amino]benzonitrile;
4-[[4-amino-5-chloro-6-[(4-cyano-2,6-dimethylphenyl)amino]-2-pyrimidinyl]amino]-benzonitrile;
4-[[5-bromo-6-[(4-cyano-2,6-dimethylphenyl)amino]-2-pyrimidinyl]amino]benzonitrile;
4-[[4-amino-5-chloro-6-(4-cyano-2,6-dimethylphenyloxy)-2-pyrimidinyl]amino]-benzonitrile; and
4-[[4-amino-5-bromo-6-(4-cyano-2,6-dimethylphenyloxy)-2-pyrimidinyl]amino]-benzonitrile; the N-oxides, the pharmaceutically acceptable addition salts, quaternary amines and the stereochemically isomeric forms thereof.

An interesting group of compounds are those compounds of formula (III) wherein one or more of the following conditions are met:
  n is 1;
  -$a^1$=$a^2$-$a^3$=$a^4$- represents a bivalent radical of formula (a-1);
  $R^1$ is hydrogen or $C_{1-4}$alkyl;
  $R^2$ is cyano; aminocarbonyl; mono- or di(methyl)aminocarbonyl; $C_{1-6}$alkyl substituted with cyano, aminocarbonyl or mono- or di(methyl)aminocarbonyl; and more in particular, $R^2$ is on the 4 position relative to the —$NR^1$— moiety;
  L is —X—$R^3$ wherein X is preferably —$NR^1$—, —O— or —S—, most preferably X is —NH—, and $R^3$ is substituted phenyl with $C_{1-6}$alkyl, halogen and cyano as preferred substituents.

Preferred compounds are those compounds of formula (III) wherein L is —X—$R^3$ wherein $R^3$ is a disubstituted phenyl group or a trisubstituted phenyl group, each substituent independently selected from chloro, bromo, fluoro, cyano or $C_{1-4}$alkyl.

Most preferred compound of formula (III) is 4-[[4-[(2,4,6-trimethylphenyl)amino]-1,3,5-triazin-2-yl]amino]benzonitrile.

Particular compounds of the present invention include 4-[[4-amino-5-bromo-6-(4-cyano-2,6-dimethylphenyloxy)-2-pyrimidinyl]amino]benzonitrile (compound A) and 4-[[4-[(2,4,6-trimethylphenyl)amino]-2-pyrimidinyl]amino]benzonitrile (compound B), their N-oxides, pharmaceutically acceptable salts and stereoisomers thereof.

The compounds of the present invention can be prepared according to art-known procedures. In particular, they are prepared according to the procedures described in EP 1002795, WO 99/50250, WO 99/50256 and WO 00/27828.

The compounds of the present invention have microbicidal activity and have the ability to prevent the transmission of HIV. In particular, they can prevent sexual or vaginal transmission of HIV by preventing either the production of infectious viral particles or infection of uninfected cells. If infected cells in sperm can reach the mucosa, the compounds of the present invention can prevent HIV infection of host cells, such as macrophages, lymphocytes, Langerhans and M cells. Thus, the present compounds prevent systemic HIV infection of a human being, exhibiting a prophylactic action against HIV. Evidence for this microbicidal activity is given in the experimental part and is based on in vivo activity of compound B in a human SCID (Severe Combined Immune Deficiency) animal model (Di Fabio et al., AIDS 2001, 15, 2231-2238) and on in vitro activity of Compound B in a model based on immature monocyte derived dendritic cells.

In addition, it has been found that the compounds of this invention have a killing effect on the *Haemophilus ducreyi* bacteria. As such, the compounds of this invention may be used in the prevention and treatment of chancroids, the venereal disease caused by this bacteria. These additional effects will even improve the effectiveness of the present compounds in preventing infection with HIV.

The compounds of the invention may be formulated into pharmaceutical compositions that can be used to apply microbicides to effectively prevent transmission of pathogens through mucosae and/or skin, more particularly to prevent the sexual or vaginal transmission of HIV. Thus, the compositions are in forms adapted to be applied to the site where sexual intercourse or related intimate contact takes place, such as the genitals, vagina, vulva, cervix, rectum, mouth, hands, lower abdomen, upper thighs, especially the vagina, vulva, cervix, and ano-rectal mucosae.

The compounds of the present invention may be formulated into pharmaceutical compositions designed for immediate release or sustained or slow release.

As appropriate topical compositions there may be cited for example gels, jellies, creams, pastes, emulsions, dispersions, ointments, films, sponges, foams, aerosols, powders, intravaginal rings or other intravaginal drug delivery systems, cervical caps, implants, patches, suppositories or pessaries for rectal, or vaginal application, vaginal or rectal or buccal tablets, mouthwashes.

To prepare the pharmaceutical compositions of this invention, an effective amount of the particular compound, optionally in addition salt form, as the active ingredient may be combined in intimate admixture with a pharmaceutically acceptable carrier, which carrier may take a wide variety of forms depending on the form of administration. For example, in preparing the compositions for topical oral administration, any of the usual pharmaceutical media may be employed such as, for example, water, glycols, oils, alcohols and the like, which are suitable for oral liquid preparations such as mouthwashes in the form of suspensions, emulsions and solutions. Solid carriers such as starches, sugars, kaolin, diluents, lubricants, binders, disintegrating agents and the like will be adequate in the case of tablets. Also included are solid form preparations which are intended to be converted, shortly before use, to liquid form preparations. In the compositions suitable for topical cutaneous administration, the carrier optionally comprises a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a cream or gel.

The active ingredient may be present in the pharmaceutical formulations as a free agent or alternatively, encapsulated into drug carriers like liposomes, nanoparticles or cyclodextrins, which encapsulation results in an increased concentration of the compounds within the microbe target site. The active ingredient may also be present as nanoparticles.

Liposomes may be present in the formulation which include, amongst others, distearoylphosphatidylcholine (DSPC), distearoylphosphatidylglycerol (DSPG), distearoylphosphatidylethanolamine-polyethylene-glycol (DSPE-PEG), dipalmitoylphosphatidylcholine (DPPC), dicetylphosphate (DP), cholesterol (CHOL), dipalmitoylphosphatidylglycerol (DPPG), and combinations thereof, such as distearoylphosphatidylcholine (DSPC): distearoylphosphatidylglycerol (DSPG); within which the active ingredient is entrapped.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy $C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD). Cyclodextrins are additionally useful in enhancing the solubility of the compounds.

The term mixed ether denotes cyclodextrin derivatives wherein at least two cyclodextrin hydroxy groups are etherified with different groups such as, for example, hydroxypropyl and hydroxyethyl.

Particularly, the present compounds may be formulated as a gel formulation comprising:
  a topically effective amount of a compound of the present invention;
  a gel-forming compound;
  a buffer;
  a pharmaceutically acceptable diluent, preferably water;
  optionally a humectant; and
  optionally a preservative.

Typical gel formulations can be prepared using natural or synthetic polymers as gelifying agents, and hydrophobic or hydrophilic liquids. Examples of gel-forming compounds commonly employed in gel formulations include polysaccharides which include cellulose derivatives, glycosaminoglycans, gums, starch (a-amylose or amylopectin), and chitosan; carboxyvinylic derivates, vinyl polymers such as polyethylenes, polyehtyelene glycols, e.g. polyethylene glycol 4500, Plastibase® (Plasticized Hydrocarbon Gel), polyacrylic acid, (Carbopols® family, e.g. Carbopol® 940), polymethacrylic acid, polyvinyl pyrrolidone and polyvinyl alcohol; polyacrylamide or polymethacrylamide polymers including clays such as bentonite, Veegum® (R. T Vanderbilt) and Laponite® (Laporte Industries); polyoxyethylene-polyoxypropylene or polyethylene oxides copolymers such as poloxamers, e.g. poloxamer 407, poloxamines; proteins, colloidal silica, soaps, silicones such as dimethylpolysiloxanes or dimeticone, hydrocarbonated bases (mixtures of parafine and vaselines).

Useful cellulose derivates include methyl cellulose, hydroxyethyl cellulose, hydroxypropyl cellulose, hydroxypropylmethyl cellulose, carboxymethyl cellulose. Useful glycosaminoglycans include hyaluronic acid, chondroitin, chondroitin-4-sulfate, heparan sulfate and heparin. Useful gums include natural and artificial gums, tragacanth, carrageenan, pectin, agar, alginic acid, dextrans. The glycosaminoglycans may be used to enhance wound healing in combination with any other gel-forming polymer such as, for example, collagen, gelatin, fibronectin. A preferred gelifying agent is hydroxyethyl cellulose, which has additionally bioadhesive properties.

Concentrations of the gel-forming compounds may be varied upon conditions such as the liquid/gel transition temperature, the physical properties sought for the gel and the pH used in the making of the formulations.

Gel forming compounds employed in the present invention are typically water-soluble polymers capable of forming a viscous aqueous solution, or non-water soluble, water-swellable polymers (e.g., collagen) that can also form a viscous solution and that gel upon contact with skin. Gelling agents suitable for use in the present invention should be stable over a wide pH range, especially over the normal acidic pH values found in the vagina.

Buffering agents are used in the gel formulation of this invention to maintain the pH of the vagina within its healthy acidic range (i.e., a pH of less than about 5 and more preferably in the range of about 3.2 to about 4.5) even in the presence of normal amounts of ejaculate. A normal acidic range in the vaginal milieu and environment assists in diminishing the activity of certain STD-causing microbes, including the HIV virus. Maintaining the normal vaginal milieu also assists in maintaining the body's natural defenses against certain STD-causing microorganisms. Examples of buffering agents include, without being limited to, lactic acid, phosphoric acid, sodium citrate, sodium hydroxide, sodium phosphate, sodium phosphate dibasic anhydrous, tartaric acid, triethanolamine, citric acid, potassium acid tartrate, benzoic acid, alginic acid, sorbic acid, fumaric acid, ascorbic acid, stearic acid, oleic acid, edetic acid, ethylenediaminetetracetic acid, acetic acid, malic acid, and the like, preferably sodium hydroxide and lactic acid, the latter being additionally a preservative and having certain antimicrobial activity.

The acids may be added as free acids, hydrates, or pharmaceutically acceptable salts. Free acids can be converted to the corresponding salts in situ (i.e., within the vagina). It is generally preferred that several buffering agents are included in the gel of this invention to provide increased buffering capacity. Even more preferably, buffering agents comprise a combination of acid and hydrogen-accepting substance that occur naturally in the human female body that, when applied to the surface of the vagina, maintains the pH level thereon at approximately the pH level of a healthy vagina. Said acid(s) may be selected from the group consisting of acetic acid, lactic acid, phosphoric acid and sulfuric acid, and combinations thereof. One of the characteristics common to each of said member in said group, is that each acid occurs naturally in the female body. Another common characteristic is each readily contributes to the formation of a buffering system, by temporarily donating hydrogen ion and accepting a cation to form a salt.

Said hydrogen-accepting substance may be selected from the group consisting of potassium hydroxide, sodium hydroxide, calcium hydroxide, potassium carbonate, sodium carbonate and calcium carbonate, and combinations thereof. One of the characteristics common to each of said member in said group, is that each substances is found naturally in the female body. Another common characteristic is each readily contributes to the formation of a buffering system, by temporarily accepting hydrogen ion and donating a cation to form a salt. Such salts may be selected from the group consisting of acetate, lactate, phosphate and sulfate, in combination with said cation from said hydrogen-accepting substance.

The gels of this invention may also include, and preferably do include, humectants. Suitable humectants include, for example, glycerol, polyethylene glycols, propylene glycols, sorbitol, triacetin, and the like. Glycerol, which is the preferred humectant, is a buffer activating component due to its capability of water absortion, or other fluid, from the vaginal environment into the gel. It is believed that such fluid intake prevents the formation of a dry film on the gel when placed within the vagina, providing additional solvent to enhance the application of the gel formulation, or to otherwise enhance its functioning.

The gels of this invention may also include, and preferably do include, a preservative, which amongst other properties, extends the shelf life of the gel formulations. Suitable preservatives include, for example, benzoic acid, sodium benzoate, methyl paraben, ethyl paraben, butyl paraben, propyl paraben, benzylalkonium chloride, phenylmercuric nitrate, chlorhexidine, benzyl alcohol, phenethyl alcohol, propylene glycol, and the like. The preferred preservatives are methyl paraben, and propyl paraben, which both also contribute to the antimicrobial capacity of the gel.

The gels of this invention are prepared using conventional gel preparation techniques. It is desirable, however, to ensure that the buffering agents are solubilized in the final product and that the entrapment of air in the gel is avoided or at least kept to a minimum. To reduce the entrapment of air in the gel, it is generally preferred that the less hydrophilic agents are added in small increments. Alternatively, the gels of this invention can also be prepared in readily dispersable solid forms (e. g., powders, tablets, and the like) which can be converted to the desired gel consistency by action of aqueous based fluids external to or within the vagina when desired. As those skilled in the art will realize, the methods for preparing the gels of this invention can be modified for batch, semi continuous, or continuous operation so long as the resulting gels have the desired and beneficial properties described herein.

The gel formulations can be combined with other active ingredients such as microbicides, antimicrobials, chemotherapeutic agents, antiinflammatory agents, spermicides or other appropriate drugs. Furthermore, microbicides or spermicides or both can be combined with liposomes (or other drug carriers) to prevent any disease of mucosae and/or skin. In addition, gel or liposome or other drug carriers formulations can also be used as carriers of vaccines against infections caused by pathogens or any disease. If desired, flavorants, scents, fragrances, and colorants can be incorporated into the gel so long as they do not interfere with the protection afforded by the gel. Indeed, incorporation of such flavorants, scents, fragrances, and colorants into the compositions of this invention may provide further protection by increasing the probability that the gel will be used during sexual activity.

In one embodiment, the gel formulation is composed of compound B, hydroxyethyl cellulose (HEC), glycerol, methyl paraben, propyl paraben, lactic acid, sodium hydroxide (for reaching a pH around 4.5), and water.

In another embodiment, the gel formulation comprises compound B, HEC with a concentration from about 0.5 to about 5% (w/w), glycerol with a concentration from about 1 to about 15% (w/w), methyl paraben with a concentration from about 0.02 to about 0.5% (w/w), propyl paraben with a concentration from about 0.005 to about 0.2% (w/w), lactic acid with a concentration from about 0.005 to about 0.5% (w/w), sodium hydroxide in sufficient quantity to achieve a pH of 4.5, and water.

In another embodiment, the gel formulation comprises compound B, HEC with a concentration from about 1 to about 3% (w/w), glycerol with a concentration from about 3 to about 7% (w/w), methyl paraben with a concentration from about 0.1 to about 0.3% (w/w), propyl paraben with a concentration from about 0.01 to about 0.03% (w/w), lactic acid with a concentration from about 0.03 to about 0.07% (w/w), sodium hydroxide in sufficient quantity to achieve a pH of 4.5, and water.

In another embodiment, any of the above gel formulations comprise compound A as a microbicide.

The present topical formulations such as the gel formulations described herein are to be used for coating different types of mucosae such as vulvar, vaginal, cervical, ano-rectal, mouth, or skin to prevent the penetration of pathogens such as viruses, bacteria, fungi, parasites, ectoparasites and mycoplasmas.

The present topical formulations such as the gel formulations described herein could, for example, be applied into the vagina by hand, suppositories, or conventional tampon or syringe techniques. The method of administering or delivering the gel into the vagina is not critical so long as an effective amount of the gel is delivered into the vagina. The present topical formulations such as the gel formulations described herein may also be used for protection during anal intercourse and can be applied using similar techniques.

For vaginal heterosexual intercourse, the present topical formulations such as the gel formulations described herein may be applied into the vagina prior to intercourse. For anal intercourse (heterosexual or homosexual), the present topical formulations such as the gel formulations described herein may be inserted into the rectum prior to intercourse. For either vaginal or anal intercourse, the present topical formulations such as the gel formulations described herein may also act as a lubricant. For added protection it is generally preferred that the present topical formulations such as the gel formulations described herein be applied before intercourse or other sexual activity and that, if appropriate, a condom be used. For even further protection, the present topical formulations such as the gel formulations described herein can be applied as soon as possible after completion of the sexual activity. Although application only after the sexual activity is less recommended, it would still be desirable afterwards if the application was not performed prior to the sexual activity for any reason (e.g., in cases of rape).

The present topical formulations such as the gel formulations described herein are highly suited for the protection of women (as well as their partners) with or without requiring the partner's knowledge of the application of these gels. In addition, reliance on the partner's claim of being STD-free, concretely HIV-free, would not be necessary, neither the agreement to use condoms or other barrier devices for protection.

The gel formulations of the present invention are additionally advantageous because they do not significantly affect or inhibit the growth characteristics of the normal vaginal flora or otherwise significantly irritate the vaginal tissue when used at inhibitory, noncytotoxic, or clinical concentrations. Significant inhibition or modifications of the vaginal flora or other irritations can lead to increased risks of infections (both STD and non-STD types) frequently mediated by ulcerations in the vagina, unusual discharges, general discomforts, and the like.

Intravaginal rings (IVR) are as well suitable drug delivery systems for the vaginal administration of the compounds of the present invention. IVRs comprise the compound(s) dispersed throughout a biocompatible elastomeric system that forms the delivery device, which preferentially takes the form of a ring. These elastomers preferably include hydrophobic material, such as silicones (organo polysiloxanes including dimethylpolysiloxanes), polyethylene-co-poly (vinyl acetate), styrene-butadiene-styrene block copolymers, polyphosphazenes, poly(isoprene), poly (isobutylene), polybutadienes, polyurethanes, nitrile rubbers, neoprene rubbers or mixtures thereof. Said IVRs can be formulated as sustained-released microbicides, resulting in an extended and stable contact time between the compound and target pathogens and cells. IVR formulations have already been described in the literature, WO02076426 all of which is herein incorporated by reference.

In order to increase the residence time of the topical pharmaceutical composition at the site of administration, it may be advantageous to include a bioadhesive in the different drug delivery systems, in particular a bioadhesive polymer. A bioadhesive may be defined as a material that adheres to a living biological surface such as for example a mucus membrane or skin tissue. The tern bioadhesive is well-known to the person skilled in the art. Thus, the present invention also relates to a pharmaceutical composition comprising a pharmaceutically acceptable carrier and as active ingredient a microbicidal effective amount of a compound of the invention characterized in that the pharmaceutical composition is bioadhesive to the site of application. Preferably, the site of application is the vagina, vulva, cervix, rectum, mouth or skin, most preferred is the vagina and the vulva.

Examples of bioadhesives which may be used in the pharmaceutical compositions of the present invention comprise polyacrylic acid derivatives, such as for example carbopol or polycarbophil, e.g. carbopol 934P, carbopol 940, polycarbophil AA1; cellulose ether derivatives such as for example hydroxypropyl methylcellulose, hydroxypropyl cellulose, hydroxyethyl cellulose, sodium carboxymethyl cellulose, chitosan; natural polymers such as for example alginates, tragacanth, inulin; pregelatinized starch; polysaccharide gums such as xanthan gum, and the like.

Alternatively, formulations of the present invention may be in the form of implants, patches, pads, injections or other preparations for achieving a percutaneous and subcutaneous delivery of the compounds to the cervical, vaginal and rectal tissues.

As already indicated within the gel specifications, the present compounds may be used in all the suitable formulations, alone or in combination with other active ingredients, such as antivirals, antibiotics, immunomodulators or vaccines. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Antiviral compounds which may be used in combination with the compounds of the invention may be known antiretroviral compounds such as suramine, pentamidine, thymopentin, castanospermine, dextran (dextran sulfate), foscarnetsodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transcriptase inhibitors such as nevirapine (11-cyclopropyl-5,11-dihydro-4-methyl-6H-dipyrido-[3,2-b:2',3'-e][1,4]diazepin-6-one), efavirenz, delavirdine, and the like; phosphonate reverse transcriptase inhibitors, e.g. tenofovir and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzo-diazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; ribonucleotide reductase inhibitors, e.g. hydroxyurea and the like.

Combinations may as well exert a synergistic effect in inhibiting HIV replication when components of the combination act on different or same sites of HIV replication, preferably on different sites. The use of such combinations may reduce the dosage of a given conventional antiretroviral agent which would be required for a desired prophylactic effect as compared to when that agent is administered as a single active ingredient. These combinations reduce potential of resistance to single agent, while minimizing any associated toxicity. These combinations may also increase the efficacy of the conventional agent without increasing the associated toxicity.

Thus, the compounds of the present invention may also be administered in combination with art-known microbicides, consequently potentiating the prophylactic effect. They can block the infection by creating a barrier between the pathogen, in this case the Human Immunodeficiency Virus, and the site at which transmission will take place, e.g. vulva, vagina; they can kill or immobilize the pathogen; they can prevent a virus from replicating once it has infected the cells lining the site of transmission, e.g. the cells that line the vaginal wall. Examples of microbicides are:

Antibiotic peptides: small protein molecules that form part of the body's first line of defense against infection. These peptides line every surface of the body—eyes, skin, lungs, tongue and intestinal tract—and kill bacteria within minutes of contact. Thus, if applied at the site of potential infection of HIV, peptides may kill pathogens before they cause infection.

Antibodies: isolated antibodies that counteract HIV are available in the literature. They may be appropriately combined with the compounds of the present invention to prevent HIV infection.

pH regulators, especially for the vagina. A natural vaginal environment is too acidic for HIV to survive, but semen decreases its acidity, allowing HIV to survive. pH regulators regulate the natural acidity of the vagina making it inhospitable for the HIV. Said regulators encompass the use of *Lactobacillus* bacteria that produce hydrogen peroxide and thereby help to keep the vaginal environment healthy and acidic. The acidic polymer BufferGel (ReProtect, LLC) is another example of a pH regulator which has in addition spermicidal activity.

Detergents and surfactants: these compounds are able to disrupt the outer shell of viruses and therefore are useful as microbicide and they can be combined with the compounds to prevent HIV infection. Examples of such detergents and surfactants are nonoxynol-9 and octoxynol-9, but all detergents and surfactants that are commonly used in shampoos, toothpastes and cleaning solutions, contact lens solutions may be equally suitable.

Coatings for the pathogen, such as Pro-2000 Gel which contains a synthetic polymer that binds to HIV, disrupting the binding of the virus to target cells.

Coatings for the site of transmission, such as for example gels. These products may prevent HIV from entering the cells by covering the site of transmission, e.g. the vaginal and vulvar epithelium. Examples, including the gel preparations described above, encompass sulphated and sulphonated polymers such as PC-515 (carrageenan), dextrin 2 sulphate, secretory leukocyte protease inhibitor (SLPI), which binds to the target cells so that they are not accessible to the virus, cyanovirin-N which also binds to the cell, prohibiting cell fusion with HIV.

In the compositions of the present invention, one or more or all of the above-listed microbicides may be combined with a compound of the invention. Thus, the present invention also relates to a pharmaceutical composition comprising a compound of the present invention and further comprising one or more components wherein the components are selected from antibiotic peptides, antibodies, pH regulators, detergents or surfactants, coatings for the pathogen, coatings for the site of administration.

One particular example of the combination of microbicides is the combination of compounds of the invention with cellulose acetate phthalate (CAP) and/or hydroxypropyl methylcellulose phthalate (HPMCP). CAP and its derivates are excipients which exhibit an additional microbicide effect. CAP formulations have already been described in the literature, EP1030547, U.S. Pat. No. 6,165,493, by Neurath et al., all of which are herein incorporated by reference.

The present invention relates also to a pharmaceutical composition as outlined hereinabove further comprising a spermicidal compound. Said compositions are able to prevent at the same time conception and HIV infection. Suitable spermicides are for example nonoxynol-9, octoxynol-9, menfegol, benzalkonium chloride, N-docasanol.

Those of skill in the prophylaxis of HIV-infection could determine the microbicidal effective amount from the test results presented here and may range from about 1 ng to about 10 mg, in particular from about 10 ng to about 1 mg, more in particular from about 100 ng to about 100 µg and preferably from about 500 ng to about 50 µg of active ingredient per application or unit dose, in particular an application or unit dose of an immediate release formulation.

It may be appropriate to apply the required dose as unit dosage forms. The volume of a unit dose, in particular the unit dose of an immediate release formulation, whether or not in a unit dosage form, may range in the case of a topical formulation from about 10 µl up to about 25 ml of topical formulation and in particular from about 1 ml up to about 10 ml of topical formulation. In the case of a gel or a cream for instance, a convenient unit dose could range between about 1 ml and about 5 ml.

For instance in the case of topical formulations, in particular topical formulations for immediate release, as mentioned herein, e.g. a gel, a cream and the like, the active ingredient may be present in a concentration ranging from about 1 nM up to about 10 mM, in particular from about 10 nM up to about 1 mM, more in particular from about 100 nM up to about 100 µM and preferably from about 1 µM to about 100 µM.

It is evident that said effective amount may be lowered or increased depending on the particular compound being used, on the response of the treated subject and/or depending on the evaluation of the physician prescribing the compounds of the instant invention.

EXAMPLES

The following examples are intended to illustrate the present invention.

Example 1

In Vitro Evaluation of the Non-Nucleoside Reverse Transcriptase Inhibitors Compound B as HIV Microbicide Cell-Free and Cell-Associated HIV Strains For experiments with CEM T cells, we used the lymphotropic SI/X4 HIV strain HTLV-III$_B$, originally obtained from R. C. Gallo and M. Popovic (NIH, Bethesda, Md.). For experiments with monocyte-derived dendritic cells (MO-DC), the monotropic NSI/R5 HIV strain Ba-L, kindly provided by the NIH AIDS Research and Reference Reagent Program (Rockville, Md.) was used. Ba-L stocks were grown and tittered on PHA/IL-2-stimulated peripheral blood mononuclear cells (PBMC) in complete medium, containing RPMI-1640 (Bio-Whittaker, Verviers, Belgium) and 10% bovine calf serum (Hyclone, Utah, US) (Peden K. Virological and Molecular Genetic Techniques for Studies of Established HIV Isolates. 1995, 21-45). The supernatant of these cultures were directly used as cell-free virus to infect MO-DC. To prepare cell-associated HIV Ba-L, non-stimulated PBMC ($2 \times 10^6$ cells/ml) were incubated overnight with $10^{-2}$ MOI (=multiplicity of infection) of HIV Ba-L in complete medium. Afterwards, cells were extensively washed, frozen in liquid nitrogen and thawed on the day of infection.

HIV Antigen Detection after Primary Culture and Calculation of EC50 Value

HIV antigen was detected using an in-house developed ELISA assay, of which the characteristics have been described (Beirnaert E, Willems B, Peeters M, Bouckaert A, Heyndrickx L, Zhong P et al. Design and Evaluation of an in-House HIV-1 (Group M and O), SIVmnd and SIVcpz Antigen Capture Assay. J Virol Methods 1998, 73: 65-70). The lower detection limit is about 200 pg/ml and the upper limit is about 25,000 pg/ml, as determined using a standard curve of Ba-L stock dilutions with known p24 content. The 50% Effective Concentration (EC50) was calculated by plotting HIV Ag concentration against drug concentration, followed by regression analysis on the linear part of the curve.

Measuring 50% Effective and 50% Cytotoxic Concentrations in CEM T Cells

As a reference system, CEM T cells (obtained from the American Type culture Collection in Rockville, Md.) were used under previously standardized conditions (Balzarini J, et al. AIDS Res Hum Retroviruses 10-4-2000, 16: 517-528). Briefly, cells were suspended at 250,000 cells/ml in RPMI-1640, supplemented with 10% fetal calf serum, 2 mM L-glutamine and 0.075% NaHCO$_3$ and infected with HTLV-III$_B$ at ~20 TCID$_{50}$. 100 µl of a 5-fold dilution series of the drugs were immediately added to 100 µl of the infected cells in 200-µl well plates. After 4 to 5 days of incubation at 37° C., the cultures were examined for syncytium formation. The EC$_{50}$ is the concentration required to inhibit syncytium formation by 50%. Cytotoxicity was evaluated and given as CC50 values, which is the concentration at which the viability of the CEM cells is decreased by 50%.

Generation of Monocyte-Derived Interstitial-Type Dendritic Cells (MO-DC) and T Cells Monocytes and lymphocytes were separated from buffy coat PBMC by counter-flow elutriation, as previously described (Van Herrewege et al. AIDS Res Hun Retroviruses 10-10-2002, 18: 1091-1102). Monocytes were further differentiated to MO-DC by culture at 37° C. and 5% CO2 during 7 days in complete medium, supplemented with 20 ng/ml GM-CSF and IL-4 (Immunosource, Zoersel, Belgium) (Sallusto et al. J Exp Med Jan. 4, 1994, 179: 1109-1118. Romani et al. J Exp Med 1-7-1994, 180: 83-93. Geissmann F, et al. Exp Med 16-3-1998, 187: 961-966). The lymphocyte fraction was frozen in liquid nitrogen and thawed on the day of infection. CD4(+) T cells were purified by positive selection, using a CD4(+) isolation kit (Dynal, Oslo, Norway), as described (Vanham et al. AIDS 20-10-2000, 14: 2299-2311. Vanham et al. AIDS 18-8-2000, 14: 1874-1876).

Pre-Treatment of HIV with Drugs, with or without Continued Treatment of MO-DC/CD4(+) T Cell Co-Cultures after Infection Cell-free HIV Ba-L was pre-incubated with a serial dilution of drug, ranging from 10,000 to 0.1 nM (final concentration), for 1 hour at 37° C. MO-DC were infected with drug-treated HIV at a multiplicity of infection (MOI) of $10^{-3}$. After 2 hours (at 37° C.), MO-DC were washed (6×) and suspended at $4 \times 10^5$ cells/ml. 50 µl of MO-DC were dispensed in a 96-well cup, together with 50 µl of autologous CD4(+) T cells ($2 \times 10^6$ cells/ml) and 100 µl of complete medium or 100 µl of drug (at the same concentration as for the pre-incubation). Half of the culture medium was refreshed twice weekly with complete medium, with or without drug. After 2 weeks of primary culture, supernatants were analysed by ELISA and cells were used for secondary cultures to check viral rescue. For experiments with cell-associated HIV, a similar set-up was used except that pre-incubated, cell-associated virus was washed before addition of MO-DC/CD4(+) T cells and remained present during the MO-DC/CD4(+) T cell co-culture.

24 Hours Drug Treatment of MO-DC/CD4(+) T Cell Co-Cultures During HIV Infection

To evaluate the effect of a 24-hours treatment, MO-DC and autologous CD4(+) T cells were suspended in complete medium at $4 \times 10^5$, resp. $2 \times 10^6$ cells/ml. Fifty µl of MO-DC and 50 µl of CD4(+) T cells were dispensed in a 96-well cup, together with 50 µl of cell-associated or cell-free virus ($10^{-3}$ MOI) and 50 µl of complete medium or 50 µl of a serial dilution of drug. After 24-hours (37° C., 5% $CO_2$), cells were washed (3×) and incubated for 2 weeks. Half of the culture medium was refreshed twice weekly with complete medium (without drug). After 2 weeks of primary culture, supernatants were analysed by ELISA and cells were used for secondary cultures to check viral rescue.

Detection of Viral Rescue: Secondary Culture and PCR Analysis

PBMC were isolated from donor buffy coats and cultured for 2 days in complete medium supplemented with 5 ng/ml IL-2 (Immunosource, Zoersel, Belgium) and 0.5 µg/ml PHA (Murex, Dartford, England). After 2 weeks of primary culture, MO-DC/CD4(+) T cell co-cultures were washed (3×) and secondary cultures were set-up by adding $1 \times 10^5$ PHA/IL-2 activated PBMC per cup. Half of the culture medium was replaced every 3-4 days with IL-2 containing medium (without drug) and supernatants as well as cells were harvested after 2 additional weeks. Supernatants were tested for HIV-Ag in ELISA. Cells were processed for HIV DNA measurement, using a PCR-based HIV proviral DNA quantitation kit, developed from Amplicor HIV-1 Monitor™ Test, version 1.5 (Roche Molecular Systems, Branchburg, USA), the modifications of which have been described (Christopherson et al. J Clin Microbiol 2000, 38: 630-634). A lower threshold of 10 HIV copies per $10^6$ cells was confirmed by using 8E5/LAV cells, containing 1 copy of proviral DNA per cell (kindly provided by the Centralized Facility for AIDS Reagents, Potters Bar, UK).

Evaluation of the Immune Suppressive Activity and Cellular Toxicity of Compound B in MO-DC/CD4(+) T Cell Co-Cultures The immune suppressive activity of compound B was measured in mixed leukocyte cultures (MLC), with MO-DC as stimulators and allogenic CD4(+) T cells as responders. Cultures of $3 \times 10^3$ MO-DC and $100 \times 10^3$ T cells were set-up in 6-fold in a 96-well plate, in the presence or absence of a dilution series of compound B. In a first part of experiments, compound B was removed after 24 hours by washing and cells were cultured for an additional 4 days. In a second part of experiments, compound B remained present during the 5-day culture period. In both set-ups, 1 µCi of [methyl-$^3$H] thymidine (TRA.120 from Amersham Pharmacia, Buckinghamshire, U.K.) was added to each well at the fifth day of culture. Plates were harvested 7 hours later and [methyl-$^3$H] thymidine incorporation was measured in a scintillation counter (Top Count™, Canberra-Packard, Zellik, Belgium) and expressed as counts per minute (CPM). The Immune Suppressive Concentration ($ISC_{50}$) is defined as the drug concentration inhibiting 50% of the lymphocyte proliferation. Cellular toxicity was evaluated microscopically by cosine staining of co-cultures of MO-DC and allogeneic CD4(+) T cells, cultured for 5 days in the presence of a dilution series of drug. Part of the harvested cells was also used for flow cytometric analysis of lymphocyte blast formation and apopotosis, based on forward and side scatter.

Reference Data on Antiviral Activity and Cellular Toxicity of Compound B

The CEM T cell line was used as a reference to determine the antiviral activity of compound B. As shown in Table 1, compound B was active in the nanomolar range and showed a low toxicity. Next to antiviral activity in CEM T cells, inhibition of HIV-1 reverse transriptase activity was measured in a cell-free assay, in which the 50% inhibitory concentration (IC50) of said compound is indicated (FIG. 1). The CEM system, using a lab T cell-line and the SI/X4 labstrain HTLV-IIIb, was not directly relevant to sexual transmission, where primary T cells, dendritic cells and NSI/R5 viruses are involved. Therefore, we focussed on prevention of NSI/R5 HIV infection in MO-DC/CD4(+) T cell co-cultures.

TABLE 1

Antiviral activity, cytotoxicity and HIV-1 RT inhibitory capacity of compound B

| Drug | Treatment | HIV | EC50 (nM)[a] | CC50 (nM)[b] | IC50 (nM)[c] |
|---|---|---|---|---|---|
| compound B | Continuous | HTLV-IIIb | 1 | 1.367 | 24 |

[a]EC50: 50% Effective Concentration, concentration required to inhibit syncytium formation of HTLV-IIIb infected CEM T cells by 50%
[b]CC50: 50% Cytotoxic Concentration, concentration at which the viability of CEM T cells is decreased by 50%
[c]IC50: 50% Inhibitory Concentration, concentration that inhibits HIV-1 reverse transcriptase activity by 50%.

Drug Treatment of MO-DC/CD4(+) T Cell Co-Cultures Prevented HIV Integration

In preliminary experiments the HIV Ba-L virus was pre-treated for 1 hour with up to 10,000 nM of compound B. The drug remained present during the 2 hours incubation of the virus with the MO-DC, but it was thoroughly washed away before addition of autologous CD4(+) T cells.

In order to study the maximal effect of the drug, pre-treatment of the virus and treatment of the cells during infection was combined with further treatment during the entire primary culture period of 2 weeks. An example of the inhibitory effects of compound B on infection with cell-associated virus is shown in Table 2. Compound B blocked infection in the primary cultures already at 10 nM, but addition of PHA/

IL-2 blasts revealed that 100 nM was needed to completely block infection and prevent proviral integration. When cell-free virus was used for infection, continuous treatment with 10 nM of compound B sufficed to completely block HIV infection, also during secondary culture (Table 3).

Next, it was investigated whether drug treatment during the first 24 hours of the primary culture could suffice to prevent viral infection and integration, as measured by ELISA and PCR respectively. As compared to continuous treatment, compound B showed to block infection at 1 log higher concentrations as used for the continuous treatment (Table 3).

TABLE 2

Inhibition of infection of MO-DC/CD4(+) T Cell co-cultures with cell-associated HIV Ba-L

| Drug | Conc (nM) | HIV Antigen (number of positive wells)[c] | | HIV proviral DNA[d] |
|---|---|---|---|---|
| | | 1° Cult.[a] | 2° Cult.[b] | (2° Cult.) |
| compound B | 10,000 | 0 | 0 | Neg |
| | 1,000 | 0 | 0 | Neg |
| | 100 | 0 | 0 | Neg |
| | 10 | 0 | 3 | 4.74 |
| No drug | 0 | 6 | 6 | 4.85 |

[a]Cell-associated HIV Ba-L was pre-incubated with drug, washed, and added to co-cultures of MO-DC and autologous CD4+ T cells. Cells were cultured for 2 weeks, in the continuous presence of drug (Primary (1°) Culture)
[b]After primary culture, cells were washed and PHA/IL-2 activated PBMCs were added and maintained in IL-2 containing medium during a secondary (2°) culture of 2 weeks (no drug present).
[c]Culture supernatant was tested for HIV antigen by ELISA. The number of antigen-positive microcultures (out of 6) is represented.
[d]After secondary culture, cells were analysed in PCR for the presence of proviral DNA, results are expressed as Log(number of DNA copies/$10^6$ cells)

TABLE 3

Conditions for Prevention of HIV infection in MO-DC/CD4(+) T Cell co-cultures

| Drug | Treatment | HIV | Conc. (nM)[a] |
|---|---|---|---|
| compound B | 24 Hours | Cell-free | 100 |
| | | Cell-associated | 1,000 |
| | Continuous | Cell-free | 10 |
| | | Cell-associated | 100 |

[a]MO-DC/CD4(+) T cell co-cultures were incubated with cell-free or cell-associated HIV and concurrently drug treated during 24 hours or continuously during 1° culture. After 1° culture, cells were washed and used for 2° cultures (no drug present). Drug concentrations that prevent replicative HIV infection, as measured by ELISA of culture supernatants and PCR of cells after 2° culture, are shown.
[b]The concentration of 10,000 nM was not used in this part of the experiment Compound B Had a Low Cellular Toxicity in CEM T Cells and a Favourable Therapeutic Index in MO-DC/CD4(+) T Cell Co-Cultures Cellular toxicity (CC50 value) in reference CEM T cells was at 1,367 nM for compound B (Table 1).

The immune suppressive activity of compound B was evaluated in mixed leukocyte cultures with MO-DC as stimulators and allogenic CD4(+) T cells as responders. If drug was present during the whole culture period, the 50% Immune Suppressive Concentration (ISC50) was about 1,500 nM. If the drug was only present during the first 24 hours, the ISC50 increased to almost 25,000 nM (Table 4). Thus, the immune suppressive activity of compound B was clearly less suppressive in the 24 hours treatment as compared to continuous treatment. In order to fully evaluate the relation of anti-viral and immune suppressive activity, the 50% antiviral activity (or EC50) values were calculated on primary drug-treated cultures of HIV-infected autologous MO-DC/CD4(+) T cell co-cultures and the therapeutic indices (TI) were determined.

The data of Table 4 shows that compound B has a favourable TI as measured in this model of primary target cells of sexual transmission.

TABLE 4

Overview of the Antiviral and Immune Suppressive Activity of compound B in co-cultures of MO-DC/CD4(+) T cells

| Drug | Treatment | HIV | EC50 (nM)[a] | ISC50 (nM)[b] | TI[c] |
|---|---|---|---|---|---|
| Comp. B | 24 hours | Cell-free | 42 | 24,886 | 592 |
| | | Cell-associated | 63 | | 395 |
| | Continuous | Cell-free | <0.1 | 1,515 | >15,150 |
| | | Cell-associated | <1[d] | | >1,515 |

[a]EC50: 50% Effective Concentration: drug concentration inhibiting 50% of HIV Ba-L replication
[b]ISC50: 50% Immune Suppressive Concentration: drug concentration inhibiting 50% of T-lymphocyte proliferation.
[c]TI: Therapeutic Index: ISC50/EC50

Additional experiments were done to evaluate if inhibition of DNA synthesis corresponded to increased mortality of T cells or only to decreased blast formation. Fifty percent inhibition of blast formation was observed at 3,916 nM. The 50% death rate of T cells was calculated at 54,222 nM.

In conclusion, prevention of HIV infection was possible against both cell-free and cell-associated NSI/R5 virus and a 24 hours treatment was sufficient. Compound B showed a high therapeutic index, based on its relative weak immune suppressive and potent anti-viral activity. These results confirmed the use of compound B as microbicide.

Example 2

Human SCID Animal Model

In order to mimic the in vivo transmission that occurs in humans, a hu-SCID animal model of vaginal transmission of HIV for the evaluation of vaginal microbicides was used (Di Fabio et al., AIDS 2001, 15, 2231-2238). Gels made up of carbopol 940 or hydroxyethyl cellulose (HEC), two water soluble polymers, were prepared containing Compound B in different concentrations (0.225 mM; 0.0225 mM or 0.00225 mM). Animals received a single intravaginal application of 25 µl of gel containing Compound B, 15-20 minutes prior to a non invasive vaginal challenge with $2 \times 10^6$ human peripheral blood lymphocytes PBL (hu-PBL) previously infected in vitro with non-syncitium (NSI) strains of HIV-1 (SF162 and 1/BX08). Cell to cell transmission was assessed by p24 production and by quantitative PCR. As a result of this study with Compound B, systemic infection was successfully inhibited.

Example 3

In Vitro Model Based on T-Cell Derived Jurkat-Tat Cells (PM-1)

Direct antiviral activity was demonstrated in a model using Jurkat-tat cells. HIV-1$^{RF}$ ($10^3$TCID$_{50}$) immobilised into 96-well coated plates were treated with test compound B for 1 hour at 37° C., compound was subsequently removed by washing with 4 volumes of PBS before co-culture with indicator cells for 8 days. Protection of infection was provided at the 100 nM concentration. Additionally, protection of infection was demonstrated at 10 nM in a parallel setup were virus was pretreated prior to addition of cells and without removal of the compound.

Example 4

Cervical Explant Model

Compound B, at a concentration of 10 nM, was able to block infection of the tissue and at a concentration of 100 nM the compound could prevent transfer of infectious virus from migratory dendritic cells to co-cultured T-cells.

Compound demonstrated good efficacy against primary HIV strains (X4, CCR5 and X4/R5) in relevant cell lines for a vaginal/rectal microbicide indication: In cervical epithelial cells (ME180) exposed to the compound during either 1 hr, 24 hrs or 5 days after which drug was removed by washing, viability of the cells was assessed with an MTT assay. Data showed no toxicity at the 50 µM concentration and some reduction of viability at 100 µM.

Example 5

Biochemical Characterization of the Interaction Between Compound B and HIV-1 Reverse Transcriptase In order to investigate the nature of the interaction between compound B and HIV-1 reverse transcriptase (HIV-1 RT), the inhibition of the RNA-dependent DNA polymerization reaction was investigated under steady state conditions. In a first experiment, the reaction velocity was determined in the presence of different concentrations of compound B and different concentrations of dGTP while the concentration of the p(rC) p(dG) complex was constant. The result showed that the binding of compound B to HIV-1 RT is non-competitive against dGTP with a Km value of 2.51 µM and a Ki of 0.033 µM.

In a second experimental the reaction velocity was determined in the presence of different concentrations of compound B and different concentrations of p(rC)p(dG) while the concentration of the substrate was constant. The result showed that the binding of compound B to HIV-1 RT is also non-competitive against p(rC)p(dG) with a Km value of 10.3 µM and a Ki of 0.028 µM. Taken together this means that the binding of compound B on HIV-1 RT is independent from the binding of nucleotide and independent from the binding of primer/template.

Example 6

Compatibility with *Lactobacilli* and Normal Vaginal Flora

Compatibility with lactobacilli and normal vaginal flora is an important requirement for a vaginal microbicide. Activity on pathogens of sexual transmitted diseases is an additional advantage. In in vitro tests for antibacterial activity of compound B, the following susceptibilities were found:

33 different *Lactobacillus* species isolated from recto-vaginal cultures of pregnant women were studied. Results showed a minimum inhibitory concentration ($MIC_{50}$) of >32 mg/L

*Hemophilus ducreyi* was inhibited by the compound with a $MIC_{50}$ of 1 mg/L and a $MIC_{90}$ of 2 mg/L Some *Neisseria gonorrhoea* strains were inhibited at clinical relevant concentrations.

Example 7

Rabbit Vaginal Irritation Test

Several formulations of the compound were used to exclude any irritation in a Rabbit Vaginal Irritation test. 24 hours after the application of 1 ml of gel/cream at different concentrations (0.1 M, 0.9 mM, 0.45 mM and 0.225 mM), vaginal epithelium was carefully examined macroscopically and microscopically. Microscopic slides of parafinized samples of different parts of the cervico-vagina were stained and analysed histologically. Macroscopic and microscopic scores obtained indicated that the formulations tested were well tolerated.

Example 8

White Rabbit Vaginal Irritation and Toxicity Study

Gel formulations of the compound B at different concentrations were used to study the exclusion of any irritation in a Rabbit Vaginal Irritation test. 10 days after the application of the gel formulations onto 6 different rabbit groups, vaginal and cervical epithelium were carefully examined by a pathologist macroscopically and histologically. The following scores were determined.

TABLE 5

Vaginal examination
Epithelial loss and atrophy accompanied by minimal or slight epithelial inflammatory cell infiltration was only seen in all female rabbits treated with Nonoxynol-9, 4%.

| | | Group/Sex | | | | | |
|---|---|---|---|---|---|---|---|
| | | 1F | 2F | 3F | 4F | 5F | 6F |
| Treatment | | Sham Control | Placebo (HEC-gel) | gel 22.5 µM | gel 225 µM | gel 10 mM | Nonoxynol 9, 4% |
| Epithelial loss and atrophy | Marked | 0 | 0 | 0 | 0 | 0 | 2 |
| | Severe | 0 | 0 | 0 | 0 | 0 | 3 |
| | Total | 0 | 0 | 0 | 0 | 0 | 5 b |
| Epithelial inflammatory infiltrate | Minimal | 0 | 0 | 0 | 0 | 0 | 3 |
| | Slight | 0 | 0 | 0 | 0 | 0 | 2 |
| | Total | 0 | 0 | 0 | 0 | 0 | 5 a | a - p < 0.05 (Fisher's exact two-tailed probability test)
b - p < 0.01 (Fisher's exact two-tailed probability test)

TABLE 6

Cervical examination
Loss and atrophy of the epithelia and luminal inflammatory cells and
cellular debris were only seen in females treated with Nonoxynol-9, 4%.

| | | Group/Sex | | | | | |
|---|---|---|---|---|---|---|---|
| | | 1F | 2F | 3F | 4F | 5F | 6F |
| Treatment | | Sham Control | Placebo (HEC-gel) | gel 22.5 μM | Gel 225 μM | gel 10 mM | Nonoxynol 9, 4% |
| Epithelial loss and atrophy | Slight | 0 | 0 | 0 | 0 | 0 | 1 |
| | Marked | 0 | 0 | 0 | 0 | 0 | 3 |
| | Total | 0 | 0 | 0 | 0 | 0 | 4 a |
| Luminal Inflammatory cells | Present | 0 | 0 | 0 | 0 | 0 | 4 |
| Total | | 0 | 0 | 0 | 0 | 0 | 4 a | a - $p < 0.05$ (Fisher's exact two-tailed probability test)

Example 9

Microbicide Gels

This example illustrates various gels with different dosages of active principle that can be prepared and used as microbicides in the prevention of HIV infection for topical administration.

TABLE 7

| 22.5 μM gel | |
|---|---|
| compound B | 0.74 mg |
| HEC | 2 g |
| Glycerol | 5 g |
| Methyl paraben | 180 mg |
| Propyl paraben | 20 mg |
| Lactic acid | 50 mg |
| Sodium hydroxide q.s. | for pH 4.5 |
| Water q.s. | 100 g |

TABLE 8

| 225 μM gel | |
|---|---|
| compound B | 7.40 mg |
| HEC | 2 g |
| Glycerol | 5 g |
| Methyl paraben | 180 mg |
| Propyl paraben | 20 mg |
| Lactic acid | 50 mg |
| Sodium hydroxide q.s. | for pH 4.5 |
| Water q.s. | 100 g |

TABLE 9

| 1 mM gel | |
|---|---|
| Compound B | 32.94 mg |
| HEC | 2 g |
| Glycerol | 5 g |
| Methyl paraben | 180 mg |
| Propyl paraben | 20 mg |
| Lactic acid | 50 mg |
| Sodium hydroxide q.s. | for pH 4.5 |
| Water q.s. | 100 g |

TABLE 10

| 10 mM gel | |
|---|---|
| compound B | 329.40 mg |
| HEC | 2 g |
| Glycerol | 5 g |
| Methyl paraben | 180 mg |
| Propyl paraben | 20 mg |
| Lactic acid | 50 mg |
| Sodium hydroxide q.s. | for pH 4.5 |
| Water q.s. | 100 g |

Various modifications and alterations to the present invention may be appreciated based on a review of this disclosure. These changes and additions are intended to be within the scope and spirit of this invention as defined by the following claims.

The invention claimed is:

1. A method for reducing transmission of or infection with HIV in a patient uninfected with HIV, comprising the step of:
   administering to said patient uninfected with HIV a medicament comprising: a compound having the formula (I) or (II);
   wherein the transmission of or infection with HIV is via sexual intercourse or related intimate contact between partners; and
   wherein a compound of formula (I) corresponds to

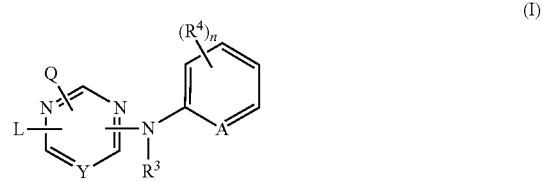

(I)

a N-oxide, a pharmaceutically acceptable addition salt or a stereochemically isomeric form thereof, wherein
Y is $CR^5$;
A is CH;
n is 1;
Q is $-NR^1R^2$ or hydrogen;

$R^1$ and $R^2$ are each independently selected from the group consisting of hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, and mono- and di($C_{1-12}$alkyl) aminocarbonyl, wherein each of said $C_{1-12}$alkyl groups may optionally and each individually be substituted with one or two substituents each independently selected from the group consisting of hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl) amino, aryl and Het; or $R^1$ and $R^2$ taken together may form pyrrolidinyl, piperidinyl, morpholinyl, azido or mono- or di($C_{1-12}$alkyl)amino$C_{1-4}$alkylidene;

$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl;

$R^4$ is cyano;

$R^5$ is hydrogen or $C_{1-4}$alkyl;

L is —$X^1$—$R^6$ or —$X^2$-Alk-$R^7$ wherein $R^6$ and $R^7$ each independently are phenyl or phenyl substituted with one, two, three, four or five substituents each independently selected from the group consisting of halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, aminocarbonyl, trihalomethyloxy and trihalomethyl;

$X^1$ and $X^2$ are each independently —$NR^3$—, —NH—NH—, —N=N—, —O—, —S—, —S(=O)— or —S(=O)$_2$—;

Alk is $C_{1-4}$alkanediyl; or

L may also be selected from the group consisting of $C_{1-10}$alkyl, $C_{3-10}$alkenyl, $C_{3-10}$alkynyl, $C_{3-7}$cycloalkyl, and $C_{1-10}$alkyl substituted with one or two substituents independently selected from the group consisting of $C_{3-7}$cycloalkyl, indanyl, indolyl and phenyl, wherein said phenyl, indanyl and indolyl may be substituted with one, two, three, four or where possible five substituents each independently selected from the group consisting of halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl;

aryl is phenyl or phenyl substituted with one, two, three, four or five substituents each independently selected from the group consisting of halo, $C_{1-6}$alkyl, $C_{1-6}$alkyloxy, cyano, nitro and trifluoromethyl;

Het is an aliphatic or aromatic heterocyclic radical; wherein said aliphatic heterocyclic radical is selected from the group consisting of pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and wherein said aromatic heterocyclic radical is selected from the group consisting of pyrrolyl, furanyl, thienyl, pyridyl, pyrimidinyl, pyrazinyl and pyridazinyl wherein each of said aromatic heterocyclic radical may optionally be substituted with hydroxy;

and, wherein a compound of formula (II) corresponds to

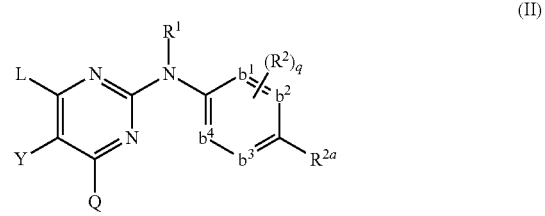

(II)

a N-oxide, a pharmaceutically acceptable addition salt, quaternary amine or a stereochemically isomeric form thereof, wherein -$b^1$=$b^2$-C($R^{2a}$)=$b^3$-$b^4$= represents a bivalent radical of formula —CH=CH—C($R^{2a}$)=CH—CH=    (b-1);

q is 0;

$R^1$ is hydrogen, aryl, formyl, $C_{1-6}$alkylcarbonyl, $C_{1-6}$alkyl, $C_{1-6}$alkyloxycarbonyl, $C_{1-6}$ alkyl substituted with formyl, $C_{1-6}$alkylcarbonyl, $C_{1-6}$alkyloxycarbonyl;

$R^{2a}$ is cyano;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

(c)

wherein each A independently is N, CH or CR$^6$;

B is NH, O, S or NR$^6$;

p is 1 or 2;

$R^6$ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, wherein each of said aliphatic group may be substituted with one or two substituents independently selected from $C_{3-7}$cycloalkyl, indolyl or isoindolyl, each optionally substituted with one, two, three or four substituents each independently selected from the group consisting of halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or L is —X—$R^3$ wherein $R^3$ is phenyl, pyridinyl, pyrimidinyl, pyrazinyl or pyridazinyl, wherein each of said aromatic rings may optionally be substituted with one, two, three, four or five substituents each independently selected from the substituents defined in $R^2$;

X is $-NR^1-$, $-NH-NH-$, $-N=N-$, $-O-$, $-C(=O)-$, $-CHOH-$, $-S-$, $-S(=O)-$ or $-S(=O)_2-$;

Q represents hydrogen, $C_{1-6}$alkyl, halo, polyhalo$C_{1-6}$alkyl or $-NR^4R^5$;

$R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of said $C_{1-12}$alkyl groups may optionally and each individually be substituted with one or two substituents each independently selected from the group consisting of hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$, aryl and Het; or $R^4$ and $R^5$ taken together may form pyrrolidinyl, piperidinyl, morpholinyl, azido or mono- or di($C_{1-12}$alkyl)amino$C_{1-4}$alkylidene;

Y represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl optionally substituted with cyano or $-C(=O)R^6$, $C_{1-6}$alkyloxy, $C_{1-6}$alkyloxycarbonyl, carboxyl, cyano, nitro, amino, mono- or di($C_{1-6}$alkyl) amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$ or aryl;

aryl is phenyl or phenyl substituted with one, two, three, four or five substituents each independently selected from the group consisting of halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy; and Het is an aliphatic or aromatic heterocyclic radical; wherein said aliphatic heterocyclic radical is selected from pyrrolidinyl, piperidinyl, homopiperidinyl, piperazinyl, morpholinyl, tetrahydrofuranyl or tetrahydrothienyl wherein each of said aliphatic heterocyclic radical may optionally be substituted with an oxo group; and wherein said aromatic heterocyclic radical is selected from the group consisting of pyrrolyl, furanyl, thienyl, pyridinyl, pyrimidinyl, pyrazinyl and pyridazinyl wherein each of said aromatic heterocyclic radical may optionally be substituted with hydroxyl.

2. A method according to claim 1, wherein the compound is

4-[[4-amino-6-[(2,6-dichlorophenyl)methyl]-2-pyrimidinyl]amino]benzonitrile;

4-[[4-[(2,4-dichlorophenyl)methyl]-6-[(4-hydroxybutyl)amino]-2-pyrimidinyl]amino]benzonitrile;

4-[[4-[(2,6-dichlorophenyl)methyl]-6-[(3-hydroxypropyl)amino]-2-pyrimidinyl]amino]benzonitrile;

N-[2-[(4-cyanophenyl)amino]-6-[(2,6-dichlorophenyl)methyl]-4-pyrimidinyl]-acetamide;

N-[2-[(4-cyanophenyl)amino]-6-[(2,6-dichlorophenyl)methyl]-4-pyrimidinyl]-butanamide;

4-[[2-amino-6-(2,6-dichlorophenoxy)-4-pyrimidinyl]amino]benzonitrile;

4-[[4-[(2,6-dichlorophenyl)methyl]-6-[(2-hydroxy-2-phenylethyl)amino]-2-pyrimidinyl]amino]benzonitrile;

4-[[4-[(2,6-dichlorophenyl)methyl]-6-[[3-(2-oxo-1-pyrrolidinyl)propyl]amino]-2-pyrimidinyl]amino]benzonitrile;

4-[[4-[(2,6-dichlorophenyl)methyl]-6-[[2-(2-hydroxyethoxy)ethyl]amino]-2-pyrimidinyl]amino]benzonitrile monohydrochloride;

4-[[4-[(2,6-dichlorophenyl)methyl]-6-[(2,3-dihydroxypropyl)amino]-2-pyrimidinyl]amino]benzonitrile;

4-[[4-[(2,6-dichlorophenyl)methyl]-6-(hydroxyamino)-2-pyrimidinyl]amino]-benzonitrile;

4-[[4-[(2-cyanoethyl)amino]-6-[(2,6-dichlorophenyl)methyl]-2-pyrimidinyl]-amino]benzonitrile;

4-[[4-[(2,6-dichlorophenyl)methyl]-6-[[2-(1-pyrrolidinyl)ethyl]amino]-2-pyrimidinyl]amino]benzonitrile;

4-[[4-amino-6-[(2,6-dichlorophenyl)methyl]-5-methyl-2-pyrimidinyl]amino]-benzonitrile;

4-[[4-[(2,4,6-trimethylphenyl)amino]-2-pyrimidinyl]amino]benzonitrile;

4-[[2-[(2,4,6-trimethylphenyl)amino]-4-pyrimidinyl]amino]benzonitrile;

4-[[4-[(2,6-dimethylphenyl)amino]-2-pyrimidinyl]amino]benzonitrile;

4-[[4-(2,4,6-trimethylphenoxy)-2-pyrimidinyl]amino]benzonitrile;

4-[[4-[(2,6-dichlorophenyl)thio]-2-pyrimidinyl]amino]benzonitrile;

4-[[4-[[2,6-dibromo-4-(1-methylethyl)phenyl]amino]-2-pyrimidinyl]amino]-benzonitrile;

4-[[4-[[2,6-dichloro-4-(trifluoromethyl)phenyl]amino]-2-pyrimidinyl]amino]-benzonitrile;

4-[[4-[(2,4-dichloro-6-methylphenyl)amino]-2-pyrimidinyl]amino]benzonitrile;

4-[[2-[(cyanophenyl)amino]-4-pyrimidinyl]amino]-3,5-dimethylbenzonitrile;

4-[[4-[(2,4-dibromo-6-fluorophenyl)amino]-2-pyrimidinyl]amino]benzonitrile;

4-[[4-[methyl(2,4,6-trimethylphenyl)amino]-2-pyrimidinyl]amino]benzonitrile;

4-[[4-[(2,4,6-trichlorophenyl)amino]-2-pyrimidinyl]amino]benzonitrile;

4-[[4-[(2,4,6-trimethylphenyl)thio]-2-pyrimidinyl]amino]benzonitrile;

4-[[4-[(2,4,6-trimethylphenyl)amino]-2-pyrimidinyl]amino]benzonitrile;

4-[[4-amino-6-[(2,4,6-trimethylphenyl)amino]-2-pyrimidinyl]amino]benzonitrile;

4-[[2-amino-6-[(2,4,6-trimethylphenyl)amino]-4-pyrimidinyl]amino]benzonitrile;

4-[[4-(2-bromo-4-chloro-6-methylphenoxy)-2-pyrimidinyl]amino]benzonitrile;

4-[[4-[(4-chloro-2,6-dimethylphenyl)amino]-2-pyrimidinyl]amino]benzonitrile;

3,5-dichloro-4-[[2-[(4-cyanophenyl)amino]-4-pyrimidinyl]amino]benzonitrile;

4-[[4-[[2,6-dichloro-4-(trifluoromethoxy)phenyl]amino]-2-pyrimidinyl]amino]benzonitrile;

4-[[4-[(2,4-dibromo-3,6-dichlorophenyl)amino]-2-pyrimidinyl]amino]benzonitrile;

4-[[4-[(2,6-dibromo-4-propylphenyl)amino]-2-pyrimidinyl]amino]benzonitrile;

4-[[4-[(4-(1,1-dimethylethyl)-2,6-dimethylphenyl)amino]-2-pyrimidinyl]amino]benzonitrile;

4-[[2-[(4-cyanophenyl)amino]-4-pyrimidinyl]oxy]-3,5-dimethylbenzonitrile;

4-[[4-[(4-chloro-2,6-dimethylphenyl)amino]-5-methyl-2-pyrimidinyl]amino]benzonitrile;

4-[[2-[(4-cyanophenyl)amino]-5-methyl-4-pyrimidinyl]amino]-3,5-dimethyl benzonitrile;
4-[[4-[[4-(1,1-dimethylethyl)-2,6-dimethylphenyl]amino]-5-methyl-2-pyrimidinyl]amino]benzonitrile;
4-[[4-[(4-bromo-2,6-dimethylphenyl)amino]-5-methyl-2-pyrimidinyl]amino]benzonitrile;
4-[[5-methyl-4-[(2,4,6-trimethylphenyl)thio]-2-pyrimidinyl]amino]benzonitrile;
4-[[4-[(2,6-dibromo-4-propylphenyl)amino]-5-methyl-2-pyrimidinyl]amino]-benzonitrile;
4-[[4-[[2,6-dibromo-4-(1-methylethyl)phenyl]amino]-5-methyl-2-pyrimidinyl]amino]benzonitrile;
4-[[2-[(4-cyanophenyl)amino]-5-methyl-4-pyrimidinyl]amino]-3,5-dimethyl benzonitrile;
4-[[4-[(phenylmethyl)amino]-2-pyrimidinyl]amino]benzonitrile;
4-[[4-amino-5-chloro-6-[(2,4,6-trimethylphenyl)amino]-2-pyrimidinyl]amino]benzonitrile;
4-[[5-chloro-4-[(2,4,6-trimethylphenyl)amino]-2-pyrimidinyl]amino]benzonitrile;
4-[[5-bromo-4-(4-cyano-2,6-dimethylphenoxy)-2-pyrimidinyl]amino]benzonitrile;
4-[[4-amino-5-chloro-6-[(4-cyano-2,6-dimethylphenyl)amino]-2-pyrimidinyl]amino]benzonitrile;
4-[[5-bromo-6-[(4-cyano-2,6-dimethylphenyl)amino]-2-pyrimidinyl]amino]-benzonitrile;
4-[[4-amino-5-chloro-6-(4-cyano-2,6-dimethylphenyloxy)-2-pyrimidinyl]amino]benzonitrile;
4-[[4-amino-5-bromo-6-(4-cyano-2,6-dimethylphenyloxy)-2-pyrimidinyl]amino]benzonitrile;
an N-oxide, a pharmaceutically acceptable addition salt, or a stereochemically isomeric form thereof, or, a quaternary amine thereof wherein the compound corresponds to a compound of formula (II).

3. A method according to claim 1,
wherein the compound is
4-[[4-amino-5-bromo-6-(4-cyano-2,6-dimethylphenyloxy)-2-pyrimidinyl]amino]benzonitrile,
4-[[4-[(2,4,6-trimethylphenyl)amino]-2-pyrimidinyl]amino]benzonitrile;
an N-oxide, or a pharmaceutically acceptable addition salt thereof, or, a quaternary amine thereof wherein the compound corresponds to a compound of formula (II).

4. A method according to claim 1,
wherein the compound is 4-[[4-[(2,4,6-trimethylphenyl)amino]-2-pyrimidinyl]amino]benzonitrile, an N-oxide, or pharmaceutically acceptable addition salt thereof.

5. A method according to claim 1,
wherein the transmission or infection is via the vagina.

6. A method according to claim 1,
wherein the medicament is in a topical form.

7. A method according to claim 1,
wherein the medicament is bioadhesive to the site of application.

8. A method according to claim 1,
wherein the medicament is in the form of a gel, jelly, cream, paste, emulsion, dispersion, ointment, film, sponge, foam, aerosol, powder, intravaginal ring, cervical cap, implant, patch, suppository, pessary, tablet or mouthwash.

9. A method according to claim 1,
wherein the medicament is in the form of an immediate release drug delivery system.

10. A method according to claim 1,
wherein the medicament is in the form of a sustained release drug delivery system.

11. A method according to claim 1,
wherein the medicament is a gel comprising:
a microbicidal effective amount of a compound as defined in claim 1,
a gel-forming compound,
a buffer,
a pharmaceutically acceptable diluent,
optionally a humectant, and
optionally a preservative.

12. A method according to claim 1,
wherein the medicament comprises 4-[[4-[(2,4,6-trimethylphenyl)amino]-2-pyrimidinyl]amino]benzonitrile, hydroxyethyl cellulose, glycerol, methyl paraben, propyl paraben, lactic acid, sodium hydroxide, and water.

13. A method according to claim 1,
wherein the medicament comprises one or more additional antiretroviral compounds.

14. A method according to claim 1,
wherein the medicament comprises one or more components selected from an antibody, a detergent or surfactant, a coating for the pathogen, a coating for the site of transmission, an antibiotic peptide or a pH regulator.

15. A method according to claim 1,
wherein the medicament comprises a spermicidal compound.

16. A method according to claim 1,
wherein the compound having the formula (I) or (II) further reduces transmission of or infection with *Haemophilus ducreyi*.

17. A method according to claim 1,
wherein the compound is
4-[[4-amino-5-bromo-6-(4-cyano-2,6-dimethylphenyloxy)-2-pyrimidinyl]amino]benzonitrile, an N-oxide, pharmaceutically acceptable addition salt, or quaternary amine thereof.

18. A method according to claim 1,
wherein the medicament is in the form of an intravaginal ring.

19. A method according to claim 4,
wherein the medicament is in the form of an intravaginal ring.

* * * * *